(12) United States Patent
Machover et al.

(10) Patent No.: US 11,596,588 B2
(45) Date of Patent: Mar. 7, 2023

(54) COMPOSITIONS FOR ALTERING THE COLOR OF HAIR

(71) Applicant: L'OREAL, Paris (FR)

(72) Inventors: Sarah Barrie Machover, New York, NY (US); Karl Wunsch, Paris (FR); Aurélie Camblong, Asnieres sur Seine (FR); Agathe Lahaye, Levallois (FR); Fabien Boulineau, Livingston, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/234,883

(22) Filed: Dec. 28, 2018

(65) Prior Publication Data

US 2019/0201309 A1 Jul. 4, 2019

Related U.S. Application Data

(60) Provisional application No. 62/611,865, filed on Dec. 29, 2017.

(51) Int. Cl.
| | | |
|---|---|---|
| *A61K 8/46* | (2006.01) |
| *A61K 8/44* | (2006.01) |
| *A61K 8/92* | (2006.01) |
| *A61K 8/362* | (2006.01) |
| *A61K 8/19* | (2006.01) |
| *A61K 8/23* | (2006.01) |
| *A61K 8/365* | (2006.01) |
| *A61K 8/41* | (2006.01) |
| *A61K 8/81* | (2006.01) |
| *A61Q 5/08* | (2006.01) |
| *A61Q 5/10* | (2006.01) |

(52) U.S. Cl.
CPC ............... *A61K 8/466* (2013.01); *A61K 8/19* (2013.01); *A61K 8/23* (2013.01); *A61K 8/362* (2013.01); *A61K 8/365* (2013.01); *A61K 8/41* (2013.01); *A61K 8/44* (2013.01); *A61K 8/447* (2013.01); *A61K 8/8176* (2013.01); *A61K 8/92* (2013.01); *A61Q 5/08* (2013.01); *A61Q 5/10* (2013.01); *A61K 2800/43* (2013.01); *A61K 2800/432* (2013.01)

(58) Field of Classification Search
CPC ........ A61Q 5/08; A61Q 5/10; A61K 2800/43; A61K 2800/432; A61K 8/466; A61K 8/44; A61K 8/92; A61K 8/447; A61K 8/362; A61K 8/19; A61K 8/23; A61K 8/365; A61K 8/41; A61K 8/8176
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,674,580 A | 4/1954 | Henkin |
| 2,850,351 A | 9/1958 | Moore et al. |
| 2,961,347 A | 11/1960 | Floyd |
| 3,142,623 A | 7/1964 | Zviak et al. |
| 3,193,464 A | 7/1965 | Edman et al. |
| 3,206,462 A | 9/1965 | McCarty |
| 3,227,615 A | 1/1966 | Korden |
| 3,288,770 A | 11/1966 | Butler |
| 3,412,019 A | 11/1968 | Hoover et al. |
| 3,472,243 A | 10/1969 | Wall et al. |
| 3,472,840 A | 10/1969 | Stone et al. |
| 3,589,978 A | 6/1971 | Kamal et al. |
| 3,632,559 A | 1/1972 | Matter et al. |
| 3,766,267 A | 10/1973 | Zak et al. |
| 3,840,656 A | 10/1974 | Kalopissis et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,003,699 A | 1/1977 | Rose et al. |
| 4,005,193 A | 1/1977 | Green et al. |
| 4,012,398 A | 3/1977 | Conner et al. |
| 4,013,787 A | 3/1977 | Vanlerberghe et al. |
| 4,025,617 A | 5/1977 | Green et al. |

(Continued)

FOREIGN PATENT DOCUMENTS

| | | |
|---|---|---|
| CN | 1383377 A | 12/2002 |
| CN | 1423548 A | 6/2003 |

(Continued)

OTHER PUBLICATIONS

International Search Report and Written Opinion dated Feb. 25, 2019 for corresponding PCT Application No. PCT/US2018/067814.
Mintel: "Conditioner," Unilever, XP055576893, Database Accession No. 3014885, Mar. 2, 2015.
"Olaplex Alleges Patent Infringement by L'OREAL re Hairbond-Building Prior to Colouring," Focus on Pigments, vol. 2017, No. 3, Mar. 31, 2017, p. 7.
Final Office Action for copending U.S. Appl. No. 15/339,035, dated May 2, 2019.

(Continued)

*Primary Examiner* — Sean M Basquill
(74) *Attorney, Agent, or Firm* — The Marbury Law Group, PLLC

(57) ABSTRACT

The present disclosure relates to color-altering compositions. The compositions comprise a hair color-altering agent and at least one carboxylic acid. Certain compositions further comprise at least one amino acid or amino sulfonic acid, and/or a salt thereof selected from the group consisting of taurine, aspartic acid, cysteine, lysine, methionine, tyrosine, phenylalanine, carnitine, a salt thereof, and a mixture thereof. Also provided are kits and methods of using said color-altering compositions.

20 Claims, 3 Drawing Sheets

(56) References Cited

U.S. PATENT DOCUMENTS

| | | |
|---|---|---|
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,412,943 A | 11/1983 | Hirota et al. |
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,734,277 A | 3/1988 | Login |
| 4,761,273 A | 8/1988 | Grollier et al. |
| 4,770,873 A | 9/1988 | Wolfram et al. |
| 4,772,462 A | 9/1988 | Boothe et al. |
| 4,777,040 A | 10/1988 | Grollier et al. |
| 4,793,992 A | 12/1988 | Mathews et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,855,130 A | 8/1989 | Konrad et al. |
| 4,906,460 A | 3/1990 | Kim et al. |
| 4,948,579 A | 8/1990 | Jacquet et al. |
| 4,970,066 A | 11/1990 | Grollier et al. |
| 5,061,289 A | 10/1991 | Clausen et al. |
| 5,085,860 A | 2/1992 | Junino et al. |
| 5,091,171 A | 2/1992 | Yu et al. |
| 5,143,518 A | 9/1992 | Madrange et al. |
| 5,196,189 A | 3/1993 | Jacquet et al. |
| 5,221,286 A | 6/1993 | Singleton et al. |
| 5,293,885 A | 3/1994 | Darkwa et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,593,662 A * | 1/1997 | Deckner ................ A61K 8/345 424/64 |
| 5,616,150 A | 4/1997 | Moeller et al. |
| 5,628,991 A | 5/1997 | Samain et al. |
| 5,635,168 A | 6/1997 | Burns et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Möckli |
| 5,750,099 A | 5/1998 | Yoshihara et al. |
| 5,766,576 A | 6/1998 | Löwe et al. |
| 5,785,962 A | 7/1998 | Hinz et al. |
| 5,811,085 A | 9/1998 | Halloran |
| 5,833,966 A | 11/1998 | Samain |
| 5,853,707 A | 12/1998 | Wells et al. |
| 5,869,068 A | 2/1999 | De Lacharriere et al. |
| 5,951,969 A | 9/1999 | Golinski et al. |
| 5,972,322 A | 10/1999 | Rath |
| 5,985,803 A | 11/1999 | Rizvi et al. |
| 6,013,250 A | 1/2000 | Cannell et al. |
| 6,015,574 A | 1/2000 | Cannell et al. |
| 6,036,966 A | 3/2000 | Youssefyeh |
| 6,090,762 A | 7/2000 | Clapperton et al. |
| 6,099,592 A | 8/2000 | Vidal et al. |
| 6,173,717 B1 | 1/2001 | Schonert et al. |
| 6,231,843 B1 | 5/2001 | Hoelzel et al. |
| 6,241,971 B1 * | 6/2001 | Fox ........................ A61K 8/19 424/47 |
| 6,284,003 B1 | 9/2001 | Rose et al. |
| 6,309,426 B1 | 10/2001 | Dias et al. |
| 6,338,741 B1 | 1/2002 | Vidal et al. |
| 6,348,189 B1 | 2/2002 | Tanabe et al. |
| 6,348,200 B1 | 2/2002 | Nakajima et al. |
| 6,358,502 B1 | 3/2002 | Tanabe et al. |
| 6,398,821 B1 | 6/2002 | Dias et al. |
| 6,458,906 B1 | 10/2002 | Torgerson et al. |
| 6,488,945 B2 | 12/2002 | Sato |
| 6,515,050 B1 | 2/2003 | Mitsuzuka et al. |
| 6,537,532 B1 | 3/2003 | Torgerson et al. |
| 6,544,500 B1 | 4/2003 | O'Toole et al. |
| 6,562,327 B1 | 5/2003 | Nguyen et al. |
| 6,569,412 B2 | 5/2003 | Yamaguchi et al. |
| 6,645,258 B2 | 11/2003 | Vidal et al. |
| 6,645,478 B2 | 11/2003 | Rollat et al. |
| 6,669,933 B2 * | 12/2003 | Duffer ................ A61K 8/9711 424/70.1 |
| 6,706,258 B1 | 3/2004 | Gallagher et al. |
| 6,730,789 B1 | 5/2004 | Birault et al. |
| 6,767,875 B1 | 7/2004 | Snyder et al. |
| 6,979,439 B1 | 12/2005 | Sakai et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,135,167 B2 | 11/2006 | Legrand et al. |
| 7,147,843 B2 | 12/2006 | Yoshida et al. |
| 7,151,079 B2 | 12/2006 | Fack et al. |
| 7,204,861 B2 | 4/2007 | Marsh et al. |
| 7,390,479 B2 | 6/2008 | Sockel et al. |
| 7,427,656 B2 | 9/2008 | Decarolis et al. |
| 7,495,037 B2 | 2/2009 | Moszner et al. |
| 7,598,213 B2 | 10/2009 | Geary et al. |
| 7,612,141 B2 | 11/2009 | Sakai et al. |
| 7,815,901 B2 | 10/2010 | Mathonneau et al. |
| 7,905,926 B2 | 3/2011 | DeGeorge et al. |
| 7,915,208 B2 | 3/2011 | Roso et al. |
| 7,931,698 B2 | 4/2011 | Simonet et al. |
| 7,972,388 B2 | 7/2011 | Hamilton et al. |
| 7,981,405 B2 | 7/2011 | Ueyama et al. |
| 8,163,861 B2 | 4/2012 | Puerta et al. |
| 8,288,329 B2 | 10/2012 | Hata |
| 8,298,519 B2 | 10/2012 | Adams et al. |
| 8,357,356 B2 * | 1/2013 | Zaeska ................ A61Q 5/10 424/70.2 |
| 8,388,701 B2 | 3/2013 | Uellner et al. |
| 8,513,200 B2 | 8/2013 | Dixon et al. |
| 8,613,913 B2 | 12/2013 | Chang et al. |
| 8,632,758 B2 | 1/2014 | Terada |
| 8,642,021 B2 | 2/2014 | Brautigam et al. |
| 8,642,659 B2 | 2/2014 | Springer et al. |
| 8,921,292 B2 | 12/2014 | Fujita et al. |
| 9,006,162 B1 | 4/2015 | Rizk |
| 9,044,409 B2 | 6/2015 | Carola et al. |
| 9,095,518 B2 | 8/2015 | Pressly et al. |
| 9,144,537 B1 | 9/2015 | Pressly et al. |
| 9,175,114 B2 | 11/2015 | Puerta et al. |
| 9,180,086 B2 | 11/2015 | Cabourg et al. |
| 9,283,156 B2 | 3/2016 | Savaides et al. |
| 9,326,926 B2 | 5/2016 | Pressly et al. |
| 9,402,796 B2 | 8/2016 | Briggs et al. |
| 9,498,419 B2 | 11/2016 | Pressly et al. |
| 9,597,273 B2 | 3/2017 | Pressly et al. |
| 9,610,241 B2 | 4/2017 | Cabourg et al. |
| 9,849,071 B2 | 12/2017 | Fack et al. |
| 9,918,923 B1 | 3/2018 | Naiberk et al. |
| 9,993,406 B2 | 6/2018 | Manneck et al. |
| 10,004,673 B2 | 6/2018 | Elsen-Wahrer et al. |
| 10,085,931 B2 | 10/2018 | Baghdadli et al. |
| 10,219,994 B2 | 3/2019 | Lechner et al. |
| 10,231,915 B2 | 3/2019 | Dreher et al. |
| 10,561,599 B2 | 2/2020 | Patterson et al. |
| 10,576,307 B2 | 3/2020 | Patterson et al. |
| 2001/0029637 A1 | 10/2001 | Nakashimada et al. |
| 2001/0042276 A1 | 11/2001 | Kawasoe et al. |

(56) References Cited

U.S. PATENT DOCUMENTS

| | | |
|---|---|---|
| 2001/0052354 A1 | 12/2001 | Nishibe et al. |
| 2002/0029429 A1 | 3/2002 | Dias et al. |
| 2002/0032933 A1 | 3/2002 | Dias et al. |
| 2002/0053110 A1 | 5/2002 | Dias et al. |
| 2002/0155081 A1 | 10/2002 | Coope |
| 2002/0189034 A1 | 12/2002 | Kitabata et al. |
| 2003/0012761 A1 | 1/2003 | Koshida et al. |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0074743 A1 | 4/2003 | Noguchi et al. |
| 2003/0083380 A1 | 5/2003 | Yu et al. |
| 2003/0152543 A1 | 8/2003 | Legrand et al. |
| 2003/0215415 A1 | 11/2003 | Mitsumatsu et al. |
| 2004/0034944 A1 | 2/2004 | Legrand et al. |
| 2004/0034946 A1 | 2/2004 | Legrand et al. |
| 2004/0067212 A1 | 4/2004 | Tokuyama et al. |
| 2004/0086475 A1 | 5/2004 | Boswell et al. |
| 2004/0088800 A1 | 5/2004 | Cotteret |
| 2004/0156877 A1 | 8/2004 | Tokuyama et al. |
| 2004/0181883 A1 | 9/2004 | Legrand et al. |
| 2004/0202689 A1 | 10/2004 | Subramanyan et al. |
| 2004/0216244 A1 | 11/2004 | Cotteret et al. |
| 2004/0228580 A1 | 11/2004 | Lee et al. |
| 2004/0241114 A1 | 12/2004 | Gupta |
| 2004/0256598 A1* | 12/2004 | Pios .............. A61K 8/411 252/299.01 |
| 2004/0258652 A1 | 12/2004 | Pascaly et al. |
| 2005/0036970 A1 | 2/2005 | Sabbagh et al. |
| 2005/0050013 A1 | 3/2005 | Ferlitsch |
| 2005/0087718 A1 | 4/2005 | Okada |
| 2005/0095215 A1 | 5/2005 | Popp |
| 2005/0176615 A1 | 8/2005 | Kinoshita et al. |
| 2005/0186164 A1 | 8/2005 | Akyuz |
| 2005/0191263 A1 | 9/2005 | Ueyama et al. |
| 2005/0193501 A1 | 9/2005 | Chan et al. |
| 2005/0201966 A1 | 9/2005 | Ueyama et al. |
| 2006/0024257 A1 | 2/2006 | Chang et al. |
| 2006/0045862 A1 | 3/2006 | Tada et al. |
| 2006/0062751 A1 | 3/2006 | Sato et al. |
| 2006/0075580 A1 | 4/2006 | Chan et al. |
| 2006/0093571 A1 | 5/2006 | Glinski |
| 2006/0135397 A1 | 6/2006 | Bissey-Beugras et al. |
| 2006/0166845 A1 | 7/2006 | Terada |
| 2006/0182702 A1 | 8/2006 | Lazzeri et al. |
| 2006/0198807 A1 | 9/2006 | Morioka |
| 2006/0228316 A1 | 10/2006 | Cannell et al. |
| 2006/0251673 A1 | 11/2006 | Hwang et al. |
| 2006/0276369 A1 | 12/2006 | Levecke et al. |
| 2007/0041921 A1 | 2/2007 | Neill et al. |
| 2007/0067924 A1 | 3/2007 | Beck et al. |
| 2007/0107142 A1 | 5/2007 | Nguyen et al. |
| 2007/0116661 A1 | 5/2007 | Mata |
| 2007/0160560 A1 | 7/2007 | Laurent et al. |
| 2007/0161543 A1 | 7/2007 | Yu et al. |
| 2007/0190008 A1 | 8/2007 | Campain et al. |
| 2007/0261594 A1 | 11/2007 | Vaskelis et al. |
| 2007/0264208 A1 | 11/2007 | Mougin et al. |
| 2008/0025937 A1 | 1/2008 | Cassier |
| 2008/0025939 A1 | 1/2008 | Cassier et al. |
| 2008/0066773 A1 | 3/2008 | Anderson et al. |
| 2008/0118458 A1* | 5/2008 | Giesen .............. A61K 8/9789 424/74 |
| 2008/0124295 A1 | 5/2008 | Duranton et al. |
| 2008/0138309 A1 | 6/2008 | Malle et al. |
| 2008/0141468 A1 | 6/2008 | Cotteret |
| 2008/0187506 A1 | 8/2008 | Carballada et al. |
| 2008/0226576 A1 | 9/2008 | Benabdillah et al. |
| 2008/0233072 A1 | 9/2008 | Bureiko et al. |
| 2008/0306025 A1 | 12/2008 | Yu et al. |
| 2009/0022681 A1 | 1/2009 | Carballada et al. |
| 2009/0041699 A1 | 2/2009 | Molenda et al. |
| 2009/0041701 A1 | 2/2009 | Taylor |
| 2009/0041713 A1 | 2/2009 | Taylor |
| 2009/0053165 A1 | 2/2009 | Brown et al. |
| 2009/0071493 A1 | 3/2009 | Nguyen et al. |
| 2009/0074683 A1 | 3/2009 | Nguyen et al. |
| 2009/0126756 A1 | 5/2009 | Syed et al. |
| 2009/0208499 A1 | 8/2009 | Yu et al. |
| 2009/0214628 A1 | 8/2009 | de Rijk |
| 2009/0252697 A1 | 10/2009 | Barbarat et al. |
| 2009/0274677 A1 | 11/2009 | Isaacs et al. |
| 2010/0004391 A1 | 1/2010 | Haddleton et al. |
| 2010/0015079 A1 | 1/2010 | Schrader |
| 2010/0081716 A1 | 4/2010 | Matsunaga et al. |
| 2010/0119468 A1 | 5/2010 | Garcia Castro et al. |
| 2010/0154140 A1 | 6/2010 | Simonet et al. |
| 2010/0158845 A1 | 6/2010 | Ellington et al. |
| 2010/0158964 A1 | 6/2010 | Cunningham et al. |
| 2010/0178267 A1 | 7/2010 | Puerta et al. |
| 2010/0189795 A1 | 7/2010 | Dreher |
| 2010/0202998 A1 | 8/2010 | Ramos-Stanbury et al. |
| 2010/0247463 A1 | 9/2010 | Yu et al. |
| 2010/0303748 A1 | 12/2010 | Hercouet |
| 2011/0056508 A1 | 3/2011 | Gross et al. |
| 2011/0061671 A1 | 3/2011 | Neplaz et al. |
| 2011/0142778 A1 | 6/2011 | Hloucha et al. |
| 2011/0150804 A1 | 6/2011 | Nojiri et al. |
| 2011/0213033 A1 | 9/2011 | Tokuyama et al. |
| 2011/0256084 A1 | 10/2011 | Dixon et al. |
| 2011/0311463 A1 | 12/2011 | Diamond et al. |
| 2012/0015894 A1 | 1/2012 | Terada |
| 2012/0022037 A1 | 1/2012 | Terada |
| 2012/0064137 A1 | 3/2012 | Kawai |
| 2012/0114583 A1 | 5/2012 | Giesen et al. |
| 2012/0118316 A1 | 5/2012 | Uellner et al. |
| 2012/0121705 A1 | 5/2012 | Paus et al. |
| 2012/0180807 A1 | 7/2012 | Flohr |
| 2012/0244082 A1 | 9/2012 | Sulzbach et al. |
| 2012/0288459 A1 | 11/2012 | Burg et al. |
| 2012/0329650 A1 | 12/2012 | Lopez-Cervantes |
| 2013/0016246 A1 | 1/2013 | Hatanaka et al. |
| 2013/0034515 A1 | 2/2013 | Stone et al. |
| 2013/0102513 A1 | 4/2013 | Terada |
| 2013/0118996 A1 | 5/2013 | Kaplan |
| 2013/0149274 A1 | 6/2013 | Nguyen et al. |
| 2013/0152959 A1 | 6/2013 | Genain et al. |
| 2013/0156716 A1 | 6/2013 | Yontz |
| 2013/0164240 A1* | 6/2013 | Schrott .............. A61K 8/893 424/70.2 |
| 2013/0172518 A1 | 7/2013 | Huang et al. |
| 2013/0216491 A1 | 8/2013 | Ogihara et al. |
| 2013/0233331 A1 | 9/2013 | Khenniche et al. |
| 2013/0233332 A1 | 9/2013 | Khenniche et al. |
| 2013/0251656 A1 | 9/2013 | Khenniche et al. |
| 2013/0266529 A1 | 10/2013 | Deconinck et al. |
| 2013/0276808 A1 | 10/2013 | Molenda et al. |
| 2013/0280199 A1 | 10/2013 | Albert et al. |
| 2013/0309190 A1 | 11/2013 | Dimotakis et al. |
| 2013/0315852 A1 | 11/2013 | Streuli |
| 2014/0120047 A1 | 5/2014 | Krueger |
| 2014/0158150 A1 | 6/2014 | Schoepgens et al. |
| 2014/0170105 A1 | 6/2014 | Chen et al. |
| 2014/0171354 A1 | 6/2014 | Miralles et al. |
| 2014/0186283 A1 | 7/2014 | Cabourg et al. |
| 2014/0196741 A1 | 7/2014 | Cabourg et al. |
| 2014/0246041 A1 | 9/2014 | Krueger |
| 2014/0248229 A1 | 9/2014 | Krueger |
| 2015/0004117 A1 | 1/2015 | Tan et al. |
| 2015/0004119 A1 | 1/2015 | Tan et al. |
| 2015/0034117 A1 | 2/2015 | Pressly et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0053228 A1 | 2/2015 | Bonauer et al. |
| 2015/0053230 A1 | 2/2015 | Myatt |
| 2015/0090285 A1 | 4/2015 | Worner et al. |
| 2015/0157544 A1 | 6/2015 | Briggs et al. |
| 2015/0252302 A1 | 9/2015 | Rieth et al. |
| 2015/0283041 A1 | 10/2015 | Benn et al. |
| 2015/0290101 A1 | 10/2015 | Pressly et al. |
| 2015/0297496 A1 | 10/2015 | Kroon et al. |
| 2015/0305469 A1 | 10/2015 | Paul |
| 2015/0313816 A1 | 11/2015 | Daubresse |

(56) References Cited

U.S. PATENT DOCUMENTS

| | | |
|---|---|---|
| 2015/0328102 A1 | 11/2015 | Pressly et al. |
| 2016/0058688 A1 | 3/2016 | Anderheggen et al. |
| 2016/0081899 A1 | 3/2016 | Pressly et al. |
| 2016/0166479 A1 | 6/2016 | Chiou et al. |
| 2016/0175238 A1 | 6/2016 | Shin et al. |
| 2016/0193129 A1 | 7/2016 | Pressly et al. |
| 2016/0235649 A1 | 8/2016 | Streuli |
| 2016/0263003 A1 | 9/2016 | Pressly et al. |
| 2016/0310394 A1 | 10/2016 | Pressly et al. |
| 2016/0331664 A1 | 11/2016 | Anderheggen et al. |
| 2016/0348037 A1 | 12/2016 | Findlay et al. |
| 2017/0007518 A1 | 1/2017 | Everaert et al. |
| 2017/0112740 A1 | 4/2017 | Schoepgens et al. |
| 2017/0112743 A1 | 4/2017 | Schoepgens et al. |
| 2017/0113071 A1 | 4/2017 | Schoepgens et al. |
| 2017/0119122 A1 | 5/2017 | Rautenberg-Groth et al. |
| 2017/0128334 A1 | 5/2017 | Schoepgens et al. |
| 2017/0128342 A1 | 5/2017 | Schoepgens et al. |
| 2017/0143611 A1 | 5/2017 | Hippe et al. |
| 2017/0151143 A1 | 6/2017 | Scheunemann et al. |
| 2017/0151144 A1 | 6/2017 | Scheunemann et al. |
| 2017/0151146 A1 | 6/2017 | Scheunemann et al. |
| 2017/0151147 A1 | 6/2017 | Scheunemann et al. |
| 2017/0151156 A1 | 6/2017 | Scheunemann et al. |
| 2017/0157011 A1 | 6/2017 | Punyani et al. |
| 2017/0165161 A1 | 6/2017 | Manneck et al. |
| 2017/0172897 A1 | 6/2017 | Kerl et al. |
| 2017/0202763 A1* | 7/2017 | Manneck ............... A61Q 5/10 |
| 2017/0246094 A1 | 8/2017 | Dreher et al. |
| 2017/0252291 A1 | 9/2017 | Lechner et al. |
| 2017/0360658 A1 | 12/2017 | Ferrari et al. |
| 2018/0055751 A1 | 3/2018 | Gevgilili et al. |
| 2018/0116942 A1 | 5/2018 | Mahadeshwar et al. |
| 2018/0140531 A1 | 5/2018 | Singer et al. |
| 2018/0140532 A1 | 5/2018 | Singer et al. |
| 2018/0280267 A1 | 10/2018 | Rughani et al. |
| 2018/0280269 A1 | 10/2018 | Rughani et al. |
| 2018/0280270 A1 | 10/2018 | Rughani et al. |
| 2018/0280271 A1 | 10/2018 | Fack et al. |
| 2018/0338895 A1 | 11/2018 | Patterson et al. |
| 2018/0338901 A1 | 11/2018 | Patterson et al. |
| 2018/0339175 A1 | 11/2018 | Patterson et al. |
| 2019/0160000 A1 | 5/2019 | Herrlein et al. |
| 2020/0129405 A1 | 4/2020 | Mitchell et al. |

FOREIGN PATENT DOCUMENTS

| | | |
|---|---|---|
| CN | 1424016 A | 6/2003 |
| CN | 1454074 A | 11/2003 |
| CN | 1678281 A | 10/2005 |
| CN | 1717215 A | 1/2006 |
| CN | 1778289 A | 5/2006 |
| CN | 1798539 A | 7/2006 |
| CN | 101282705 A | 10/2008 |
| CN | 101495087 A | 7/2009 |
| CN | 101686920 A | 3/2010 |
| CN | 101843561 A | 9/2010 |
| CN | 101966136 A | 2/2011 |
| CN | 102056896 A | 5/2011 |
| CN | 102166163 A | 8/2011 |
| CN | 102231974 A | 11/2011 |
| CN | 102281864 A | 12/2011 |
| CN | 102361627 A | 2/2012 |
| CN | 102397232 A | 4/2012 |
| CN | 102451117 A | 5/2012 |
| CN | 103356395 A | 10/2013 |
| CN | 103998099 A | 8/2014 |
| CN | 104066419 A | 9/2014 |
| CN | 104159567 A | 11/2014 |
| CN | 104519962 A | 4/2015 |
| CN | 105267066 A | 1/2016 |
| CN | 105902403 A | 8/2016 |
| CN | 105902404 A | 8/2016 |
| CN | 106265109 A | 1/2017 |
| DE | 1220969 B | 7/1966 |
| DE | 2225541 A1 | 12/1973 |
| DE | 2359399 A1 | 6/1975 |
| DE | 3843892 A1 | 6/1990 |
| DE | 4133957 A1 | 4/1993 |
| DE | 4300320 A1 | 7/1994 |
| DE | 19543988 A1 | 5/1997 |
| DE | 29722990 U1 | 5/1999 |
| DE | 10051773 A1 | 4/2002 |
| DE | 10051774 A1 | 4/2002 |
| DE | 20208254 U1 | 8/2002 |
| DE | 10 2004 052480 A1 | 5/2006 |
| DE | 10 2007 039745 A1 | 2/2009 |
| DE | 20 2015 104742 U1 | 10/2015 |
| DE | 10 2014 213317 A1 | 1/2016 |
| DE | 10 2015 223828 A1 | 9/2016 |
| DE | 10 2015 221460 A1 | 5/2017 |
| DE | 20 2017 001430 U1 | 7/2017 |
| DE | 102016200688 A1 | 7/2017 |
| EP | 0122324 A1 | 10/1984 |
| EP | 0159628 A2 | 10/1985 |
| EP | 0286261 A2 | 10/1988 |
| EP | 0298684 A2 | 1/1989 |
| EP | 0299764 A2 | 1/1989 |
| EP | 0437114 A1 | 7/1991 |
| EP | 0512879 A2 | 11/1992 |
| EP | 0636358 A1 | 2/1995 |
| EP | 0714954 A2 | 6/1996 |
| EP | 0770375 A1 | 5/1997 |
| EP | 0855178 A2 | 7/1998 |
| EP | 0978272 A1 | 2/2000 |
| EP | 1118319 A1 | 7/2001 |
| EP | 1174112 A2 | 1/2002 |
| EP | 1216023 B1 | 4/2005 |
| EP | 1541117 A1 | 6/2005 |
| EP | 1570832 A1 | 9/2005 |
| EP | 1216022 B1 | 4/2006 |
| EP | 1690524 A2 | 8/2006 |
| EP | 1779896 A2 | 5/2007 |
| EP | 1810657 A1 | 7/2007 |
| EP | 2123250 A1 | 11/2009 |
| EP | 2165697 A1 | 3/2010 |
| EP | 2229933 A1 | 9/2010 |
| EP | 2295029 A1 | 3/2011 |
| EP | 2460511 A1 | 6/2012 |
| EP | 2471504 A1 | 7/2012 |
| EP | 2478892 A1 | 7/2012 |
| EP | 1510197 B1 | 3/2016 |
| FR | 1492597 A | 8/1967 |
| FR | 1583363 A | 10/1969 |
| FR | 2162025 A | 7/1973 |
| FR | 2252840 A1 | 6/1975 |
| FR | 2270846 A1 | 12/1975 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2789895 A1 | 8/2000 |
| FR | 2789896 A1 | 8/2000 |
| FR | 2801308 A1 | 5/2001 |
| FR | 2841129 A1 | 12/2003 |
| FR | 2886136 A1 | 12/2006 |
| FR | 2939030 A1 | 6/2010 |
| FR | 2944441 A1 | 10/2010 |
| FR | 2966352 A1 | 4/2012 |
| FR | 2975899 A1 | 12/2012 |
| FR | 2975900 A1 | 12/2012 |
| GB | 713675 A | 8/1954 |
| GB | 741307 A | 11/1955 |
| GB | 773559 A | 4/1957 |
| GB | 1026978 A | 4/1966 |
| GB | 1125794 A | 8/1968 |
| GB | 1153196 A | 5/1969 |
| GB | 1260451 A | 1/1972 |
| GB | 1546809 A | 5/1979 |
| GB | 1584364 A | 2/1981 |
| JP | S60-158105 A | 8/1985 |
| JP | 63-154611 A | 6/1988 |

(56) References Cited

FOREIGN PATENT DOCUMENTS

| | | |
|---|---|---|
| JP | S63-255214 A | 10/1988 |
| JP | 02-019576 A | 1/1990 |
| JP | H02-138110 A | 5/1990 |
| JP | 05-163124 A | 6/1993 |
| JP | H07-069847 A | 3/1995 |
| JP | 08-198732 A | 8/1996 |
| JP | H08-509478 A | 10/1996 |
| JP | 2000-229821 A | 8/2000 |
| JP | 2001-081013 A | 3/2001 |
| JP | 2002-097115 A | 4/2002 |
| JP | 2002-105493 A | 4/2002 |
| JP | 2002-121121 A | 4/2002 |
| JP | 2002-356408 A | 12/2002 |
| JP | 2002-363048 A | 12/2002 |
| JP | 2003-095876 A | 4/2003 |
| JP | 2003-516335 A | 5/2003 |
| JP | 2004-026976 A | 1/2004 |
| JP | 2005-060398 A | 3/2005 |
| JP | 2005-154348 A | 6/2005 |
| JP | 2006-219493 A | 8/2006 |
| JP | 2006-327994 A | 12/2006 |
| JP | 2008-169183 A | 7/2008 |
| JP | 2008-189686 A | 8/2008 |
| JP | 2009-007283 A | 1/2009 |
| JP | 2009-536619 A | 10/2009 |
| JP | 2010-155823 A | 7/2010 |
| JP | 2012-515218 A | 7/2012 |
| JP | 2013-500328 A | 1/2013 |
| JP | 2013-028564 A | 2/2013 |
| JP | 2015-086211 A | 5/2015 |
| JP | 2016-003185 A | 1/2016 |
| JP | 2017-095451 A | 6/2017 |
| JP | 2018-514570 A | 6/2018 |
| KR | 10-2001-0039848 A | 7/2001 |
| KR | 2003-0003970 A | 1/2003 |
| KR | 10-2004-0098688 A | 11/2004 |
| KR | 10-2006-0059564 A | 6/2006 |
| KR | 10-2012-0062511 A | 6/2012 |
| KR | 10-2016-0064420 A | 6/2016 |
| RU | 2144945 C1 | 1/2000 |
| RU | 2229281 C1 | 5/2004 |
| WO | 93/00882 A1 | 1/1993 |
| WO | 93/08787 A2 | 5/1993 |
| WO | 94/08969 A1 | 4/1994 |
| WO | 94/08970 A1 | 4/1994 |
| WO | 95/01152 A1 | 1/1995 |
| WO | 95/01772 A1 | 1/1995 |
| WO | 95/15144 A1 | 6/1995 |
| WO | 96/15765 A1 | 5/1996 |
| WO | 97/24106 A1 | 7/1997 |
| WO | 98/56333 A1 | 12/1998 |
| WO | 99/11226 A1 | 3/1999 |
| WO | 99/66793 A1 | 12/1999 |
| WO | 01/35912 A1 | 5/2001 |
| WO | 01/47486 A1 | 7/2001 |
| WO | 01/52005 A1 | 7/2001 |
| WO | 02/19976 A1 | 3/2002 |
| WO | 02/32383 A1 | 4/2002 |
| WO | 02/32386 A2 | 4/2002 |
| WO | 02/055034 A2 | 7/2002 |
| WO | 2004/002411 A2 | 1/2004 |
| WO | 2004/019858 A2 | 3/2004 |
| WO | 2005/058258 A1 | 6/2005 |
| WO | 2006/011771 A1 | 2/2006 |
| WO | 2006/134051 A1 | 12/2006 |
| WO | WO-2007003307 A1 | 1/2007 |
| WO | 2007/038733 A1 | 4/2007 |
| WO | 2009/024936 A2 | 2/2009 |
| WO | 2010/015517 A2 | 2/2010 |
| WO | 2010/049434 A2 | 5/2010 |
| WO | 2011/134785 A2 | 11/2011 |
| WO | 2012/033813 A2 | 3/2012 |
| WO | 2012/080321 A2 | 6/2012 |
| WO | 2012/084532 A2 | 6/2012 |
| WO | 2012/084876 A2 | 6/2012 |
| WO | 2012/164064 A1 | 12/2012 |
| WO | 2013/092080 A1 | 6/2013 |
| WO | 2013/136480 A1 | 9/2013 |
| WO | 2014/016407 A1 | 1/2014 |
| WO | 2014/072490 A1 | 5/2014 |
| WO | 2014/118212 A1 | 8/2014 |
| WO | 2014/125452 A1 | 8/2014 |
| WO | 2014/144076 A1 | 9/2014 |
| WO | 2014/167508 A1 | 10/2014 |
| WO | 2014/207097 A1 | 12/2014 |
| WO | 2015/017768 A1 | 2/2015 |
| WO | 2015/026994 A1 | 2/2015 |
| WO | 2015/033351 A1 | 3/2015 |
| WO | 2015/058942 A1 | 4/2015 |
| WO | 2015/069823 A1 | 5/2015 |
| WO | 2015/075064 A2 | 5/2015 |
| WO | 2015/118357 A2 | 8/2015 |
| WO | 2015/175986 A2 | 11/2015 |
| WO | 2016/005114 A1 | 1/2016 |
| WO | 2016/005144 A1 | 1/2016 |
| WO | 2016/058749 A1 | 4/2016 |
| WO | 2016/069877 A1 | 5/2016 |
| WO | 2016/091492 A1 | 6/2016 |
| WO | 2016/098870 A1 | 6/2016 |
| WO | 2016/100885 A1 | 6/2016 |
| WO | 2016/102543 A1 | 6/2016 |
| WO | 2016/120642 A1 | 8/2016 |
| WO | 2016/161360 A1 | 10/2016 |
| WO | 2016/179017 A1 | 11/2016 |
| WO | 2016/198203 A1 | 12/2016 |
| WO | 2017/041903 A1 | 3/2017 |
| WO | 2017/041905 A1 | 3/2017 |
| WO | 2017/041906 A1 | 3/2017 |
| WO | 2017/041907 A1 | 3/2017 |
| WO | 2017/041908 A1 | 3/2017 |
| WO | 2017/041909 A1 | 3/2017 |
| WO | 2017/041910 A1 | 3/2017 |
| WO | 2017/059646 A1 | 4/2017 |
| WO | 2017/085117 A1 | 5/2017 |
| WO | 2017/091794 A1 | 6/2017 |
| WO | 2017/091796 A1 | 6/2017 |
| WO | 2017/091797 A1 | 6/2017 |
| WO | 2017/091800 A1 | 6/2017 |
| WO | 2017/102855 A1 | 6/2017 |
| WO | 2017/102936 A1 | 6/2017 |
| WO | 2017/116465 A1 | 7/2017 |
| WO | 2017/196299 A1 | 11/2017 |
| WO | WO-2017207198 A1 | 12/2017 |
| WO | 2018/081399 A1 | 5/2018 |
| WO | WO-2018085478 A1 | 5/2018 |

OTHER PUBLICATIONS

International Preliminary Report on Patentability for counterpart Application No. PCT/US2017/058495, dated May 9, 2019.
Notice of Allowance for copending Application No. 15/778,803, dated Jun. 3, 2019.
Extended European Search Report for counterpart Application No. 16869327.3-1114, dated Jun. 4, 2019.
Mintel: "Detox 7 Day Cure Purifying Serum," XP055593471, Jeanne Gatineau, Feb. 11, 2013.
Extended European Search Report for counterpart Application No. 1689330.7-1114, dated Jul. 5, 2019.
Extended European Search Report for counterpart Application No. 16869326.5-1114, dated Jun. 26, 2019.
Translation of Mexican Office Action for counterpart Application No. MX/a/2018/005829, dated Jun. 13, 2019.
Non-Final Office Action for copending U.S. Appl. No. 15/339,035, dated Aug. 20, 2019.
Mexican Office Action for counterpart Application No. MX/a/2017/013983, dated Jul. 2, 2019.
Notice of Allowance for copending U.S. Appl. No. 16/042,478, dated Sep. 25, 2019.
Non-Final Office Action for copending U.S. Appl. No. 15/778,807, dated Sep. 30, 2019.
Brazilian Office Action for counterpart Application No. BR112017023380-0, dated Oct. 10, 2019.

(56) References Cited

OTHER PUBLICATIONS

Brazilian Office Action for counterpart Application No. BR112018010381-0, dated Nov. 25, 2019.
Brazilian Office Action for counterpart Application No. BR112018010357-8, dated Nov. 25, 2019.
Mexican Office Action for counterpart Application No. MX/a/2018/005829, dated Oct. 5, 2019.
Brazilian Office Action for counterpart Application No. BR112018010344, dated Nov. 25, 2019.
Mexican Office Action for counterpart Application No. MX/a/2017/013983, dated Dec. 16, 2019.
Japanese Office Action for counterpart Application No. 2018-526844, dated Dec. 23, 2019.
Japanese Office Action for counterpart Application No. 2018-526845, dated Dec. 23, 2019.
Japanese Office Action for counterpart Application No. 2018-546409, dated Dec. 23, 2019.
Brazilian Written Opinion for counterpart Application No. BR112018010341, dated Nov. 25, 2019.
Non-Final Office Action for counterpart Japanese Application No. 2018-546408, dated Jan. 6, 2020.
Mintel: "Tonic," Dr. Kurt Wolff, Dr. Wolff Plantur 39, ID# 3133037, Apr. 2015.
Mintel: "Conditioner," LG Household & Health Care, Beyond Professional, ID# 3240637, Jun. 2015.
Russian Office Action for counterpart Application No. 2018114758/04, dated Dec. 13, 2019.
Translated Notification of Reasons for Refusal for counterpart KR Application No. 10-2018-7017668, dated Jan. 21, 2020.
Translated Office Action for counterpart RU Application No. 2017134681/04(0060925), dated Dec. 30, 2019.
Non-Final Office Action for copending U.S. Appl. No. 15/778,805, dated Feb. 12, 2020.
Final Office Action for copending Application No. 15/778,807, dated Mar. 13, 2020.
Final Office Action for copending U.S. Appl. No. 15/339,035, dated Apr. 10, 2020.
Non-Final Office Action for copending U.S. Appl. No. 16/273,787, dated Apr. 9, 2020.
International Search Report and Written Opinion for counterpart Application No. PCT/US2017/059827, dated Jun. 28, 2018.
"LAMESOI-1® PO 65 Datasheet," Retrieved from the internet on Jun. 7, 2018, http://e-applications.basf-ag.de/data/basf-pcan/pds2/pds2-web.nsf.
Non-Final Office Action for copending U.S. Appl. No. 15/356,967, dated May 3, 2017.
Final Office Action for copending U.S. Appl. No. 15/356,967, dated Dec. 4, 2017.
Non-Final Office Action for copending U.S. Appl. No. 15/356,967, dated Aug. 24, 2018.
Final Office Action for copending U.S. Appl. No. 15/356,967, dated Apr. 11, 2019.
Non-Final Office Action for copending U.S. Appl. No. 15/356,967, dated Feb. 21, 2020.
International Search Report and Written Opinion for counterpart Application No. PCT/US2017/059817, dated Feb. 6, 2018.
Non-Final Office Action for copending U.S. Appl. No. 15/357,056, dated Apr. 16, 2020.
Non-Final Office Action for copending U.S. Appl. No. 15/942,042, dated Jan. 24, 2020.
ALS "Cocamidopropyl betaine," printed 2020; https://www.caslab.com/Cocamidopropyl_betaine_CAS_61789-40-0.
International Search Report and Written Opinion for counterpart Application No. PCT/US2018/025466, dated Jul. 9, 2018.
International Preliminary Report on Patentability for counterpart Application No. PCT/US2018/025466, dated Oct. 1, 2019.
International Search Report and Written Opinion for counterpart Application No. PCT/US2018/025448, dated Jul. 9, 2018.
International Preliminary Report on Patentability for counterpart Application No. PCT/US2018/025448, dated Oct. 1, 2019.
International Search Report and Written Opinion for counterpart Application No. PCT/US2018/025431, dated Jun. 20, 2018.
International Preliminary Report on Patentability for counterpart Application No. PCT/US2018/025431, dated Oct. 1, 2019.
International Search Report and Written Opinion for counterpart Application No. PCT/US2018/025418, dated Jun. 21, 2018.
International Preliminary Report on Patentability for counterpart Application No. PCT/US2018/025418, dated Oct. 1, 2019.
Notice of Allowance for copending U.S. Appl. No. 15/604,152, dated Oct. 2, 2019 (now U.S. Pat. No. 10,561,599).
Non-Final Office Action for copending U.S. Appl. No. 15/604,152, dated Jun. 13, 2019.
Olaplex with relaxers, OLAPLEX™, pp. 1-2, Apr. 11, 2017, https://olaplex.es/olaplex-with-relaxers/.
Relaxers, resource Library, Olaplex Education, pp. 1-2, Apr. 11, 2017, https://help.olaplex.com/detail/relaxers.
Noticeof Allowability for copending U.S. Appl. No. 15/604,152, dated Dec. 10, 2019.
International Search Report and Written Opinion for counterpart Application No. PCT/US2018/034366, dated Jul. 25, 2018.
Anonymous: "Curly Hair Conditioner," Mintel, GNPD, XP002782449, 2015, pp. 1-2.
Corrected Noticeof Allowability for copending U.S. Appl. No. 15/604,189, dated Dec. 11, 2019.
Notice of Allowance for copending U.S. Appl. No. 15/604,189, dated Oct. 22, 2019 (now U.S. Pat. No. 10,576,307).
Non-Final Office Action for copending U.S. Appl. No. 15/604,189, dated Apr. 8, 2019.
International Search Report and Written Opinion for counterpart Application No. PCT/US2018/034371, dated Nov. 16, 2018.
Mintel: "Hydrating Hair Colour," Garnier, Jan. 2017, pp. 1-6.
Mintel, "Masque Force Architecte Reconstructing Masque," L'Oreal, Feb. 2012, pp. 1-6.
Final Office Action for copending U.S. Appl. No. 15/603,889, dated Jul. 12, 2019.
Non-Final Office Action for copending U.S. Appl. No. 15/603,889, dated Jan. 2, 2019.
International Search Report and Written Opinion for counterpart Application No. PCT/US2018/034378, dated Jul. 24, 2018.
Final Office Action for copending U.S. Appl. No. 16/234,883, dated Mar. 11, 2020.
Non-Final Office Action for copending U.S. Appl. No. 16/234,883, dated Sep. 16, 2019.
Final Office Action for copending U.S. Appl. No. 16/176,350, dated Apr. 8, 2020.
Non-Final Office Action for copending U.S. Appl. No. 16/176,350, dated Nov. 14, 2019.
International Search Report and Written Opinion for counterpart Application No. PCT/US2019/059002, dated Feb. 4, 2020.
Translated Korean Notification of Reason for Refusal for counterpart Application No. KR10-2017-7034789, dated May 19, 2020.
Final Office Action for copending U.S. Appl. No. 15/942,042, dated Jun. 1, 2020.
Translated Japanese Notice of Reasons for Refusal by Application No. 2017-557074, dated Jun. 1, 2020.
Non-Final Office Action for copending U.S. Appl. No. 15/942,085, dated Jun. 19, 2020.
Non-Final Office Action for copending U.S. Appl. No. 15/941,916, dated Jun. 24, 2020.
Shiseido Super Mild Hair Care—Shampoo and Conditioner Refill Set. https://web.archive.org/web/20160326190615/http://www.truenu.com/TR/Shiseido-Super-Mild-Hair-Care-Shampoo-Conditioner-Refill-Set-Two-400ml-Refill-Pouches-Details.html. Published Mar. 26, 2016.
Non-Final Office Action for copending U.S. Appl. No. 15/941,965, dated Jul. 15, 2020.
Third Party Observation for counterpart Application No. EP 20160869330, dated Jun. 26, 2020.
Third Party Observation for counterpart Application No. EP 20160869326, dated Jul. 2, 2020.
Third Party Observation for counterpart Application No. EP 20160869327, dated Jul. 2, 2020.

(56) References Cited

OTHER PUBLICATIONS

Translation of Japanese Office Action for counterpart Application No. 2018-526844, dated Aug. 3, 2020.
Copending U.S. Appl. No. 15/484,625, filed Apr. 11, 2017 (WO2016179017A1).
Copending U.S. Appl. No. 15/484,663, filed Apr. 11, 2017 (WO2017091794A1).
Copending U.S. Appl. No. 15/339,035, filed Oct. 31, 2016 (WO2018081399A1).
International Search Report and Written Opinion for counterpart Application No. PCT/US2016/030172, dated Sep. 19, 2016.
International Search Report and Written Opinion for counterpart Application No. PCT/US2016/063724, dated Feb. 2, 2017.
International Search Report and Written Opinion for counterpart Application No. PCT/US2016/063727, dated Feb. 3, 2017.
International Search Report and Written Opinion for counterpart Application No. PCT/US2016/063732, dated Feb. 3, 2017.
International Search Report and Written Opinion for counterpart Application No. PCT/US2016/063728, dated Feb. 1, 2017.
Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperle Haircare, Database Record No. 3645337, Feb. 2016.
Mintel: "Conditioner," Laperle Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Database Record No. 1507159, Mar. 2011.
Mintel: "Post-Service Perfector," Redken, Database Record No. 4326453, Nov. 2016.
Mintel: "Step 3-Conditioner," L'OREAL, Database Record No. 4353779, Oct. 2016.
Mintel: "Step 3-Conditioner," L'OREAL, Database Record No. 4609117, Feb. 2017.
International Preliminary Report on Patentability for counterpart Application No. PCT/US2016/30172, dated Jun. 19, 2017.
Petition for Post-Grant Review of U.S. Pat. No. 9,498,419, filed Jan. 31, 2017, with Exhibits.
Non-Final Office Action for copending U.S. Appl. No. 15/484,625, mailed Jun. 21, 2017.
Final Office Action for copending U.S. Appl. No. 15/484,625, dated Nov. 14, 2017.
Non-Final Office Action for copending U.S. Appl. No. 15/484,663, dated Jun. 21, 2017.
Final Office Action for copending U.S. Appl. No. 15/484,663, dated Nov. 28, 2017.
Non-Final Office Action for copending U.S. Appl. No. 15/339,035, dated Jan. 10, 2018.
International Search Report for counterpart Application No. PCT/US2017/058495, dated Jan. 5, 2018.
Third Party Submission for U.S. Appl. No. 15/484,663, filed Feb. 28, 2018 with attachments.
Pressly, Eric et al., U.S. Appl. No. 61/994,709, filed May 16, 2014 and became publicly available on Nov. 19, 2015.
Estetica: the hairstyling professional magazine, (http://estetica.it/int/a/schwarzkopf-professional-launches-fibreplex), "Schwarzkopf Professional Launches Fibreplex®," published Sep. 23, 2015 reporting that Fibreplex was launched during Sep. 2015.
Fibreplex® No. 1 Product Label.
Fibreplex® No. 1 Material Safety Data Sheet.
International Preliminary Report on Patentability for counterpart Application No. PCT/US2016/063727, dated Jun. 7, 2018.
International Preliminary Report on Patentability for counterpart Application No. PCT/US2016/063732, dated Jun. 7, 2018.
International Preliminary Report on Patentability for counterpart Application No. PCT/US2016/063728, dated Jun. 7, 2018.
Non-Final Office Action for copending U.S. Appl. No. 15/484,625, dated Jun. 20, 2018.
International Preliminary Report on Patentability for counterpart Application No. PCT/US2016/063724, dated Jun. 7, 2018.
Non-Final Office Action for copending U.S. Appl. No. 15/339,035, dated Oct. 5, 2018.
Notice of Allowance for copending U.S. Appl. No. 15/484,625, dated Oct. 31, 2018.
Bayraktar, V.N., "Organic Acids Concentration in Wine Stocks After *Saccharomyces cerevisiae* Fermentation," Biotechnologia Acta, vol. 6, No. 2, Jan. 1, 2013, pp. 97-106.
Supplementary European Search Report for counterpart Application No. EP16789846, dated Oct. 30, 2018.
Communication Pursuant to Rules 70(32) and 70A(2) EPC for counterpart Application No. EP16789846, dated Jan. 23, 2019.
Written Opinion for counterpart Application No. EP16789846, dated Jan. 23, 2019.
Supplementary Extended Search Report and Written Opinion for counterpart European U.S. Appl. No. 16/869,324, dated Apr. 25, 2019.
Mintel: "Conditioner," Unilever, XP-55576888, Database accession No. 1419415, Oct. 21, 2010.
Chinese Office Action for counterpart Application No. 201880021603.6, dated Mar. 2, 2021.
Translation of Chinese Office Action for counterpart Application No. 201680039105.5, dated Feb. 4, 2021.
European Office Action for counterpart Application No. 16869330.7-1112, dated Feb. 4, 2021.
European Office Action for counterpart Application No. 16869324.0-1112, dated Feb. 18, 2021.
Translation of Chinese Office Action for counterpart Application No. 201680079800.4, dated Feb. 24, 2021.
Supplemental Search Report for Chinese counterpart Application No. 201680079800.4, dated Feb. 18, 2021.
Non-Final Office Action for copending U.S. Appl. No. 16/455,139, dated Jan. 26, 2021.
Translation of Third Party Observation for Application No. 2018-546408, dated Sep. 11, 2020.
European Office Action for counterpart Application No. 16869327.3-1112, dated Dec. 18, 2020.
Translation of Russian Office Action for counterpart Application No. 2018114758/04, dated Dec. 21, 2020.
Final Office Action for copending U.S. Appl. No. 15/941,916, dated Mar. 10, 2021.
Translation of Chinese Office Action for counterpart Application No. 201680079110.9, dated Aug. 11, 2020.
Ruiming, Li, "Hairdressing Technology," China Railway Publishing House, Jun. 30, 2015, pp. 112-113.
Translation of Mexican Office Action for counterpart Application No. MX/a/2018/005829 dated Jul. 13, 2020.
Mascolo Group, label.m Anti-Frizz Mist, MINTEL GNPD, record ID5618119, published Apr. 2018, p. 1-5.
Federici Brands, Color WOW Dream Coat Supernatural Spray, MINTEL GNPD, record ID5637153, published Apr. 2018, p. 1-2.
Garnier, Garnier Fructis Sleek & Shine Moroccan Sleek Oil Treatment, MINTEL GNPD, record ID1876023, published Sep. 2012, p. 1-2.
Ouai, Leave-In Conditioner, MINTEL GNPD, record ID5781323, published Jun. 2018, p. 1-2.

(56) References Cited

OTHER PUBLICATIONS

Redken, Redken Pillow Proof Express Treatment Primer, MINTEL GNPD, record ID5117339, published Sep. 2017, p. 1-4.
Redken, Redken Pillow Proof Express Primer Time-Saving Blowdry Primer with Heat Protection, MINTEL GNPD, record ID6117357, published Nov. 2018, p. 1-2.
Redken, Redken Pillow Proof Time-Saving Blowdry Primer with Heat Protection, MINTEL GNPD, record ID4537755, published Jan. 2017, p. 1-3.
Copending U.S. Appl. No. 16/455,139, "Hair Treatment Compositions and Methods for Treating Hair," filed Jun. 27, 2019.
Translation of Russian Office Action for counterpart Application No. 2017134681-04, dated Aug. 17, 2020.
Translation of Chinese Office Action for counterpart Application No. 201680079800.4, dated Aug. 24, 2020.
Search Report for Chinese Application No. 201680079800.4, dated Aug. 24, 2020.
Translation of Chinese Office Action for counterpart Application No. 201680079773.0, dated Aug. 21, 2020.
Search report for counterpart Chinese Application No. 201680079773.0, dated Aug. 21, 2020.
Translation of Japanese Office Action for counterpart Application No. 2018-546409, dated Sep. 7, 2020.
Translation of Chinese Office Action for counterpart Application No. 201680079774.5, dated Sep. 1, 2020.
Fridman, R.A., "Technology of Cosmetics," publ. of "Food Industry," 1964, pp. 3-6, 297-308, 411-428 and 44 1-466 (translation).
Zefirova, N.S., "Big Russian Encyclopedia," Chemical Encylopedia, 1995, vol. 4, pp. 183-185 (translation).
Third Party Submission for U.S. Appl. No. 16/712,326 with attachments, filed Sep. 8, 2020.
Mexican Office Action for counterpart Application No. MX/a/2017/013983, dated Sep. 15, 2020.
Non-Final Office Action for copending U.S. Appl. No. 16/176,350, dated Sep. 30, 2020.
Non-Final Office Action for copending U.S. Appl. No. 15/778,807, dated Oct. 9, 2020.
Japanese Notice of Reasons for Refusal for counterpart Application No. 2019-553190, dated Oct. 27, 2020.
Translation of Korean Notice of Last Preliminary Rejection for counterpart Application No. 10-2018-7017668, dated Oct. 21, 2020.
Non-Final Office Action for copending U.S. Appl. No. 15/942,042, dated Nov. 12, 2020.
Final Office Action for copending U.S. Appl. No. 15/356,967, dated Nov. 17, 2020.
Final Office Action for copending U.S. Appl. No. 15/357,056, dated Nov. 19, 2020.
Japanese Office Action for counterpart Application No. 2018-546408, dated Dec. 7, 2020.
Japanese Notice of Reasons for Rejection for counterpart Application No. 2019-553559, dated Dec. 1, 2020.
Japanese Notice of Reasons for Rejection for counterpart Application No. 2019-564945, dated Dec. 1, 2020.
Final Office Action for copending U.S. Appl. No. 15/941,965, dated Apr. 5, 2021.
Non-Final Office Action for copending U.S. Appl. No. 16/234,883, dated Sep. 17, 2021.
Final Office Action for copending U.S. Appl. No. 15/942,085, dated Sep. 21, 2021.
Final Office Action for copending U.S. Appl. No. 15/603,889, dated Jan. 6, 2022.
Final Office Action for copending U.S. Appl. No. 15/942,042, dated May 12, 2021.
Non-Final Office Action for copending U.S. Appl. No. 15/942,085, dated Jun. 8, 2021.
Tetrasodium Etidronate, https://uk.lush.com/ingredients/tetrasodium-etidronate. Published Mar. 28, 2020.
Shoup, F.K., et al., "Amino Acid Composition of Wheat Varieties and Flours Varying Widely in Bread-Making Potentialities," Journal of Food Science, vol. 31, Issue 1, published Jan. 1966, pp. 94-101.

"Oxy Cream," Makki Cosmetics, https://www.makkicosmetics.com/makki/showProductjsp?productID=Oxy25030&brandID=Makki, published Jun. 30, 2016.
Non-Final Office Action for copending U.S. Appl. No. 15/339,035, dated Jun. 25, 2021.
Non-Final Office Action for copending U.S. Appl. No. 15/603,889, dated Jun. 25, 2021.
Partial Translation of Office Action for copending MX Application No. MX/a/2017/013983, dated Apr. 4, 2021.
Translation of Chinese Office Action for counterpart Application No. 201680079773, dated Apr. 14, 2021.
Translation of Japanese Office Action for counterpart Application No. 2017-557074, dated May 31, 2021.
Translation of Japanese Notice of Reasons for Refusal for counterpart Application No. 2019-553190, dated Jun. 12, 2021.
Final Office Action for copending Application No. 15/778,807, dated Jul. 21, 2021.
Non-Final Office Action for copending U.S. Appl. No. 15/356,967, dated Jul. 22, 2021.
Copending U.S. Appl. No. 17/228,040, Titled: "Compositions for Altering the Color of Hair," Inventors: Kimberly Dreher et al., filed Apr. 12, 2021.
Copending U.S. Appl. No. 17/403,327, Titled: Hair Treatment Compositions, Methods, and Kits for Treating Hair, Inventors: Barbara Mitchell et al., filed Aug. 16, 2021.
Final Office Action for copending U.S. Appl. No. 16/455,139, dated Aug. 11, 2021.
Chinese Office Action for counterpart Application No. 201880021603.6, dated Dec. 8, 2021.
Chinese Office Action for counterpart Application No. 201880034065.4, dated Dec. 22, 2021.
Translation of Chinese Office Action for counterpart Application No. 201680039105.5, dated Jan. 14, 2022.
Translation of Chinese Office Action for counterpart Application No. 201880034056.6, dated Dec. 28, 2021.
Non-Final Office Action for copending U.S. Appl. No. 15/941,965, dated Aug. 22, 2022.
Non-Final Office Action for copending U.S. Appl. No. 15/942,085, dated Aug. 23, 2022.
Third Party Submission for copending U.S. Appl. No. 17/403,327, filed Jun. 27, 2022.
Non-Final Office Action for copending U.S. Appl. No. 15/942,042, dated May 23, 2022.
Translation of Second Chinese Office Action for counterpart Application No. 201880034056.5, dated May 30, 2022.
Translation of First Chinese Office Action for counterpart Application No. 201880084390.1, dated Jun. 30, 2022.
European Office Action for counterpart Application No. 16789846.9-1 109, dated Jul. 6, 2022, translation.
Korean Notice of Final Rejection for counterpart KR Application No. 10-2021-7019867, dated Jul. 22, 2022, translation.
Translation of Japanese Notice of Reasons for Rejection of Correction for counterpart Opposition No. 2022-700161, dated Aug. 18, 2022.
Translation of Korean Office Action for counterpart Application No. 10-2021-7020401, dated Aug. 25, 2022.
Non-Final Office Action for copending U.S. Appl. No. 15/339,035, dated Oct. 27, 2022.
Translation of Chinese Office Action for counterpart Application No. 2019800675489, dated Oct. 12, 2022.
Non-Final Office Action for copending U.S. Appl. No. 15/356,967, dated Dec. 30, 2022.
Third Party Submission for copending U.S. Appl. No. 17/694,821, dated Dec. 19, 2022.
Translation of Notice of Reasons for Rejection of counterpart Japanese Application No. 2022-020688, dated Jan. 10, 2023.
Translation of Chinese Decision on Rejection for counterpart CN Application No. 201880034056.5, dated Jan. 9, 2023.
Non-Final Office Action for copending U.S. Appl. No. 17/356,131, dated Jan. 19, 2023.

\* cited by examiner

US 11,596,588 B2

COMPOSITIONS FOR ALTERING THE COLOR OF HAIR

CROSS-REFERENCE TO RELATED APPLICATIONS

This application claims priority to U.S. Provisional Patent Application No. 62/611,865, filed on Dec. 29, 2017, entitled "COMPOSITIONS FOR ALTERING THE COLOR OF HAIR," the entirety of which is herein incorporated by reference.

FIELD

The present disclosure generally relates to compositions for use in bleaching and/or coloring the hair.

BACKGROUND

The process of changing the color of hair, can involve depositing an artificial color onto the hair which provides a different shade or color to the hair, and/or lifting the color of the hair, such as lightening the color of dark hair to lighter shades.

In general, hair lightening or color lifting compositions and hair dyeing compositions possess an alkalinity such that these compositions have a pH value of above 7, typically being at pH 9 and above, and may generally require the presence of an alkalizing agent such as ammonia or an ammonia gas-generating compound and/or an amine or ammonium-based compound in amounts sufficient to make such compositions alkaline. This alkalizing agent causes the hair shaft to swell, thus allowing active agents into the hair.

Imparting a color change or color effect on hair can be done using permanent and semi-permanent or temporary hair coloring products. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as mono-ethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Semi-permanent dyeing uses direct dyes, which are non-ionic or ionic dyes and colored compounds capable of producing a more or less pronounced change of the natural color of the hair, resistant to shampoo-washing several times. These dyes may or may not be used in the presence of an oxidizing agent. In contrast with oxidation dye precursors, a direct dye is a relatively voluminous molecule that does not penetrate easily into the core of the fiber.

The process of lifting the color of hair, generally also requires the use of compositions that comprise at least one oxidizing agent (e.g., hydrogen peroxide). Such oxidizing agents enter the hair shaft and react with melanin in the hair, thereby lightening the color of the hair. Additional agents, such as persulfate salts, may be added to accelerate the process.

While such hair compositions can effectively alter the color of hair, these chemical treatments can severely damage the hair fibers. Thus, in order to reduce or avoid the drawbacks mentioned above, as well as to improve the cosmetic performance of the treatment compositions, the use of new and additional ingredients and novel combinations of ingredients are continuously sought which can help prevent, ameliorate or reverse damage.

Nevertheless, the choice of ingredients or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can effectively treat the hair, e.g. lift the color of hair and/or deposit color onto hair in an efficient manner, while providing other cosmetic advantages such as shine, conditioning, fiber strength, and/or a healthy appearance to the hair, but avoiding or minimizing damage to the hair.

SUMMARY

One aspect of the invention pertains to a hair color-altering composition. In one or more embodiments, the composition comprises:
  at least one amino acid or amino sulfonic acid, and/or a salt thereof selected from the group consisting of taurine, aspartic acid, cysteine, lysine, methionine, tyrosine, phenylalanine, carnitine, aminomethane sulfonic acid, aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, a salt thereof, and a mixture thereof;
  at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, and combinations thereof;
  a hair color-altering agent selected from the group consisting of oxidizing agents, oxidative dyes, direct dyes and combinations thereof; and
  water.

In some embodiments, the at least one amino acid or amino sulfonic acid and/or salt thereof is taurine and/or a salt thereof. In one or more embodiments, the composition comprises from about 0.01 wt. % to about 10 wt. % of the at least one amino acid or amino sulfonic acid and/or a salt thereof. In some embodiments, the at least one amino acid or amino sulfonic acid and/or a salt thereof is present in an amount of from about 0.01 wt. % to about 5 wt. %. In one or more embodiments, the composition comprises at least 0.01 wt. % to about 10 wt. % of the at least one carboxylic acid and/or a salt thereof. In some embodiments, the at least one carboxylic acid and/or a salt thereof is present in an amount of from about 0.01 wt. % to about 7 wt. %. In one or more embodiments, the at least one carboxylic acid and/or a salt thereof is a tricarboxylic acid and/or a salt thereof. In some embodiments, the tricarboxylic acid and/or salt thereof is selected from the group consisting of citric acid, isocitric acid, aconitic acid, propane-1,2,3-tricarboxylic acid, trimesic acid, a salt thereof, and a mixture thereof. In one or more embodiments, the tricarboxylic acid and/or salt thereof is citric acid, and/or a salt thereof. In some embodiments, the composition further comprises one or more alkalizing agents. In one or more embodiments, the one or more alkalizing agents is selected from alkali metal carbonates, alkali metal phosphates, organic amines, hydroxide base compounds, and combinations thereof. In some embodiments, the one or more alkalizing agents is selected from the group consisting of ammonium hydroxide, monoethanolamine and combinations thereof. In one or more embodiments, the composition further comprises one or more fatty compounds selected from the group consisting oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters or diesters of ethylene glycol and fatty acids, esters of fatty acids and fatty alcohols, esters of short chain alcohols and fatty acids, esters of fatty alcohols, hydroxy-substituted fatty acids, waxes, triglyceride compounds, lanolin, ceramide, and mixtures thereof. In some embodiments, the composition further comprises one or more cationic polymers. In one or more embodiments, the one or more cationic polymers are selected from the group consisting of poly(methacryloyloxyethyl trimethylammonium chloride), polyquaternium-37, quaternized cellulose derivatives, polyquaternium-4, polyquaternium-6, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some embodiments, the hair color-altering agent comprises and oxidative dye.

Another aspect of the invention pertains to a hair cosmetic composition for lifting or altering the color of keratinous substrates. In one or more embodiments, the composition comprises:
  a. at least one alkalizing agent selected from alkali metal carbonates, alkali metal phosphates, organic amines, hydroxide base compounds, and mixtures thereof;
  b. at least two fatty substances selected from alkanes comprising 6 to 16 carbon atoms, fatty alcohols, esters of fatty acids, esters of fatty alcohol, non-silicone oils, non-silicone waxes, silicones and mixtures thereof;
  c. at least one surfactant selected from anionic surfactants, nonionic surfactants and mixtures thereof;
  d. at least one cationic polymer;
  e. at least one solvent selected from water, organic solvents and mixtures thereof; and
  f. at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, and combinations thereof.

In some embodiments, the composition further comprises at least one amino acid or amino sulfonic acid, and/or a salt thereof selected from the group consisting of taurine, aspartic acid, cysteine, lysine, methionine, tyrosine, phenylalanine, carnitine, aminomethane sulfonic acid, aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid. In one or more embodiments, the at least one amino acid or amino sulfonic acid comprises taurine. In one or more embodiments, the composition further comprises at least one hair color-altering agent. In some embodiments, the at least one hair color-altering agent comprises at least one oxidative dye. In one or more embodiments, the at least one carboxylic acid and/or a salt thereof is present in an amount of about 0.05 wt. % to about 10 wt. % by total weight of the composition. In one or more embodiments, the at least one alkalizing agent is selected from the group consisting of monoethanolamine, ammonium hydroxide, and mixtures thereof. In some embodiments, the cationic polymer is selected from the group consisting of poly (methacryloyloxyethyl trimethylammonium chloride), polyquaternium-37, quaternized cellulose derivatives, polyquaternium-4, polyquaternium-6, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In one or more embodiments, the at least two fatty substances are selected from mineral oil, cetearyl alcohol, oleyl alcohol, glycol distearate, hydrogenated vegetable oil, and mixtures thereof. In some embodiments, the hair color-altering composition does not comprise a thickener, cellulose or gum. In one or more embodiments, the at least one surfactant comprises an anionic surfactant selected from oleic acid and/or a nonionic surfactant selected from deceth-3, oleth-30 and combinations thereof.

Figures 1A, 1B:
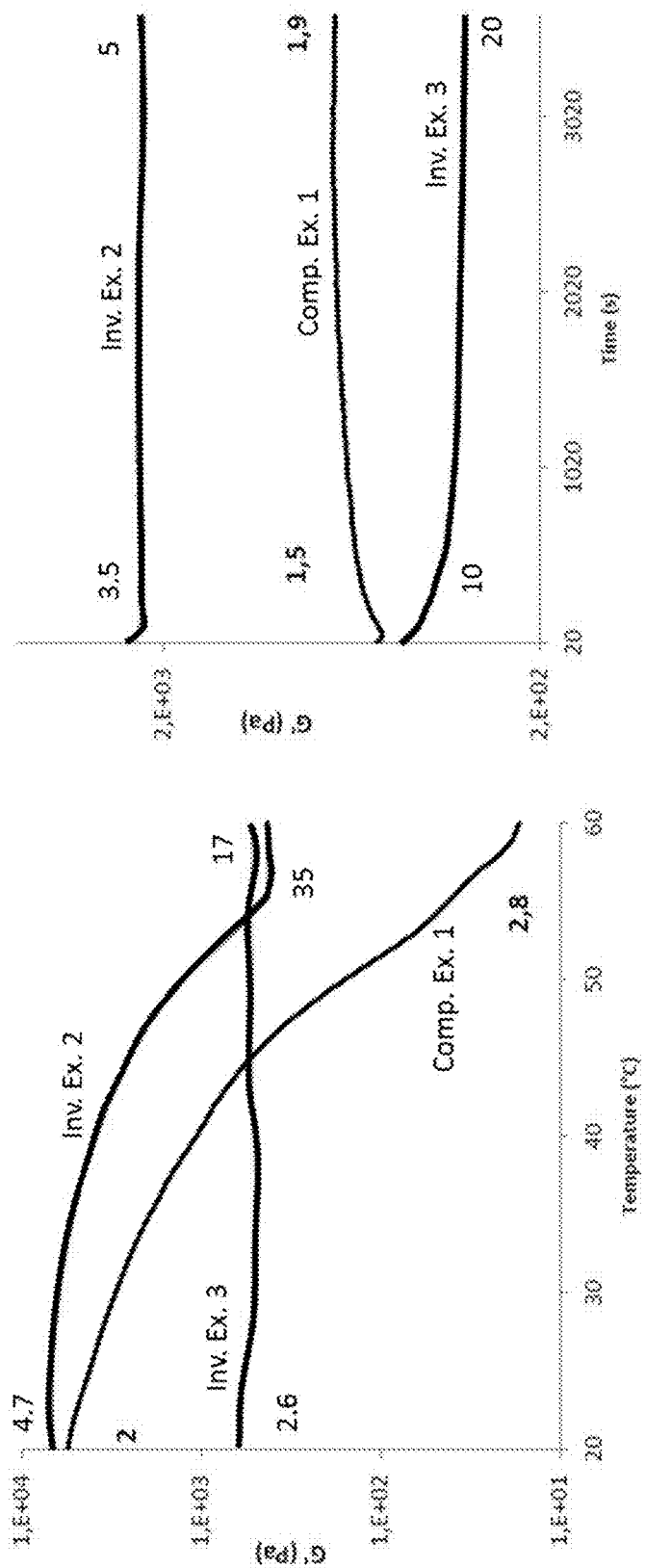
FIGS. 1A-B show the evolution of elastic modulus (G') measured as a function of time and temperature of inventive and comparative formulas.

It should be understood that the various aspects are not limited to the arrangements and instrumentality shown in the drawings.

DETAILED DESCRIPTION

One aspect of the invention relates to hair color-altering compositions. The hair color-altering compositions at least comprise a hair color-altering agent and a carboxylic acid. In one or more embodiments, hair color-altering composition comprises
- at least one amino acid or amino sulfonic acid, and/or a salt thereof selected from the group consisting of taurine, aspartic acid, cysteine, lysine, methionine, tyrosine, phenylalanine, carnitine, a salt thereof, and a mixture thereof;
- at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, and combinations thereof;
- a hair color-altering agent selected from the group consisting of oxidizing agents, oxidative dyes, direct dyes and combinations thereof; and
- water.

In some embodiments, the hair color-altering composition comprises
- at least one alkalizing agent selected from alkali metal carbonates, alkali metal phosphates, organic amines, hydroxide base compounds, and mixtures thereof;
- at least two fatty substances selected from alkanes comprising 6 to 16 carbon atoms, fatty alcohols, esters of fatty acids, esters of fatty alcohol, non-silicone oils, non-silicone waxes, silicones and mixtures thereof;
- at least one surfactant selected from anionic surfactants, nonionic surfactants and mixtures thereof;
- at least one cationic polymer;
- at least one solvent selected from water, organic solvents and mixtures thereof; and
- at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, and combinations thereof.

The presence of citric acid has surprisingly been found to positively affect the rheology characteristics of certain hair color-altering compositions, particularly in combination with several other ingredients (e.g., certain surfactants an fatty substances). Additionally, citric acid/or taurine may also provide protect the hair from damage when undergoing color alteration.

The hair color-altering compositions of the instant disclosure can be in a variety of forms. For example, in many instances, the hair color-altering compositions are in the form of a liquid, gel, lotion, crème, and/or spray. The hair color-altering compositions may be packaged in a variety of different containers, such as, for example, a ready-to-use container. Non-limiting examples of useful packaging include tubes, jars, caps, unit dose packages, and bottles, including squeezable tubes and bottles.

Amino Acid/Amino Sulfonic Acid

In some embodiments, the hair color-altering compositions comprise an amino acid or amino sulfonic acid. Amino acids are simple organic compounds containing both a carboxylic acid group (—COOH) and an amino group (—NH$_2$). Amino sulfonic acids are simple organic compounds containing both a sulfonic acid group (—SO$_2$OH) and an amino group (—NH$_2$). Accordingly; the amino acids and amino sulfonic acids may be selected from compounds of Formula (I) and compounds of Formula (II):

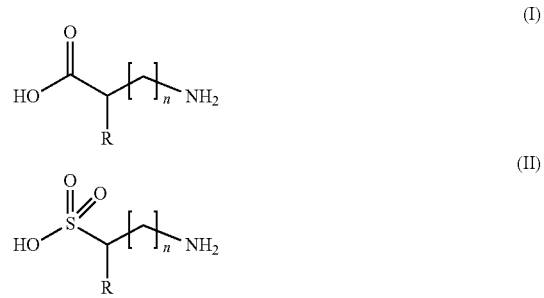

wherein R represents a hydrogen atom, a linear or branched, preferably linear, $C_1$-$C_5$ alkyl group, said alkyl group being optionally substituted with at least one group chosen from hydroxyl, —C(O)—OH, —S(O)$_2$—OH, —C(O)—O$^-$ and M$^+$, and S(O)$_2$—O$^-$ and M$^+$, with M$^+$ representing a cationic counter-ion such as an alkali metal, alkaline earth metal, or ammonium, and n is 0 or 1. In the hair color-altering compositions containing them, the amino acids and amino sulfonic acids may be in their non-ionized form (I) and (II) or in their ionized or betaine form (I') and (II'):

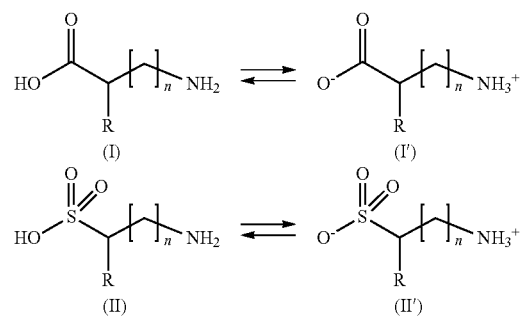

wherein "R" and "n" are as defined above. The one or more amino acids and/or amino sulfonic acids may also be in their conjugate base form (Ib) and (IIb).

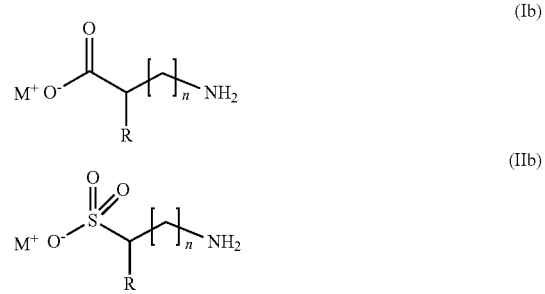

wherein "R" and "n" are as defined above.

Well-known amino adds include the twenty amino acids that form the proteins of living organisms (standard proteinogenic amino acids): alanine, arginine, asparagine, aspartic add, cysteine, glutamic acid, glutamine, glycine, histidine, isoleucine, leucine, lysine, methionine, phenylalanine, proline, serine, threonine, tryptophan, tyrosine, and valine. The amino acids of the instant disclosure, however, are not limited to the standard proteinogenic amino adds.

Non-limiting examples of amino sulfonic acids include aminomethane sulfonic acid, aminoethane sulfonic acid (taurine), aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, and a mixture thereof.

In some cases, charged amino acids may be used. Non-limiting examples of charged amino acids include arginine, lysine, aspartic acid, and glutamic acid. In some cases, polar amino acids are useful. Non-limiting examples of polar amino acids include glutamine, asparagine, histidine, serine, threonine, tyrosine, cysteine, methionine, and tryptophan.

In some cases, hydrophobic amino acids may be employed. Non-limiting examples of hydrophobic amino acids include alanine, isoleucine, leucine, phenylalanine, valine, proline, and glycine.

In some instances, the hair color-altering compositions include at least one amino acid or an amino sulfonic acid, and/or a salt thereof, selected from the group consisting of glycine, alanine, serine, beta-alanine, taurine, sodium glycinate, sodium alaninate, sodium serinate, lithium beta-alanine, sodium taurate, and a mixture thereof.

In some cases, the hair color-altering compositions include only amino acid(s) and/or salt(s) thereof, only sulfonic acid(s) and/or salt(s) thereof, or a mixture of both amino acids and sulfonic acids, and/or salts thereof, for example, one or more amino acids and one or more amino sulfonic acids, and/or salts thereof, for example, those selected from the group consisting of aspartic acid, cysteine, glycine, lysine, methionine, proline, tyrosine, phenylalanine, carnitine, taurine, a salt thereof, and a mixture thereof.

In some cases, the hair color-altering compositions include at least taurine (2-aminoethane sulfonic acid) and/or a salt thereof.

The total amount of the at least one amino acid or amino sulfonic acid, and/or salt thereof, is at least 0.01 wt. %, based on the total weight of the hair color-altering composition. The total amount of the at least one amino acid or amino sulfonic acid, and/or salt thereof, may be from about 0.01, 0.02, 0.03, 0.04, 0.05, 0.06, 0.07, 0.08, 0.09, 1, 2, 3, 4, 5, 6, 7, 8 or 9 wt. % to about 0.02, 0.03, 0.04, 0.05, 0.06, 0.07, 0.08, 0.09, 1, 2, 3, 4, 5, 6, 7, 8, 9 or 10 wt. % of the total composition. For example, the at least one amino acid or amino sulfonic acid and/or a salt thereof may be present from about 0.01 wt. % to about 10 wt. % of the total composition, or more particularly from about 0.01 wt. % to about 5 wt. % of the total composition.

Carboxylic Acid

The hair color-altering compositions may include at least one carboxylic acid, and/or a salt thereof, typically in an amount of at least 0.01 wt. %, based on the total weight of the hair color-altering composition.

A non-polymeric mono, di, and/or tricarboxylic acid is an organic compound having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of mono-carboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair color-altering compositions include at least lactic acid and/or or a salt thereof.

Non-limiting examples of di-carboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair color-altering compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair color-altering compositions include at least citric acid and/or a salt thereof.

In one or more embodiments, the hair color-altering composition comprise at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, and combinations thereof.

The total amount of the at least one non-polymeric mono, di, or tricarboxylic acid, and/or a salt thereof, is at least 0.01 wt. %, based on the total weight of the hair color-altering composition. In some cases, the total amount of the at least one non-polymeric mono, di, or tricarboxylic acid, and/or salt thereof, ranges from about 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8 or 9 wt. % to about 1, 2, 3, 4, 5, 6, 7, 8, 9 or 10 wt. % by total weight of the composition.

Hair Color-Altering Agent

The hair color-altering compositions may comprise a hair color-altering agent selected from the group consisting of oxidizing agents, oxidative dyes, direct dyes.

In embodiments comprising oxidizing agents, the at least one oxidizing agent may be chosen, for example, from peroxides, persulfates, perborates, percarbonates, alkali metal bromates, ferricyanides, peroxygenated salts, alkali metal carbonates, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In one embodiment, the oxidizing agent can be hydrogen peroxide present in an aqueous solution whose titer may range from 1 to 40 volumes, such as from 5 to 40 volumes or such as from 5 to 20 volumes.

In another embodiment, the oxidizing agent can be a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. In certain embodiments, the oxidizing agent is hydrogen peroxide.

In general, the oxidizing agent will be present in an amount ranging from about 0.05 to about 50% by weight, such as from about 0.1% to about 30% by weight, from about 0.1% to about 20% by weight, or from about 1% to about 10% by weight, based on the total weight of the developer composition or solution or system in which it is present.

In embodiments comprising oxidation dyes, the oxidation dyes are generally chosen from one or more oxidation bases optionally combined with one or more couplers. By way of example, the oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxyphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-☐-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly, oxidation bases can be selected from 3-aminopyrazolo-[1,5-a]-pyridines and preferably substituted on carbon atom 2 by:
 (a) one (di)($C_1$-$C_6$)(alkyl)amino group wherein said alkyl group can be substituted by at least one hydroxy, amino, imidazolium group;
 (b) one heterocycloalkyl group containing from 5 to 7 members chain, and from 1 to 3 heteroatomes, potentially cationic, potentially substituted by one or more ($C_1$-$C_6$)alkyl, such as di($C_1$-$C_4$)alkylpiperazinium; or
 (c) one ($C_1$-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl) -3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropylpyrazole, 4-amino-5-(2'-aminoethyl)amino -1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof. 4,5-Diamino-1-(β-methoxyethyl)pyrazole may also be used. A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a] pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used. 4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Compositions and/or systems according to embodiments of the disclosure may optionally further comprise one or more couplers advantageously chosen from those conventionally used in the dyeing or coloring of keratinous substrates.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may be present in an amount ranging from about 0.001% to 10% by weight, such as from about 0.005% to 5% by weight, relative to the total weight of the system or composition comprising the system in which it is present.

The coupler(s), if they are present, may be present in an amount ranging from about 0.001% to 10% by weight, such as from about 0.005% to 5% by weight, relative to the total weight of the system or composition comprising the system in which it is present.

Compositions according to embodiments of the disclosure may optionally comprise one or more synthetic or natural direct dyes, for example chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Preferably direct dyes are cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| Het⁺—C(R$^a$)=N—N(R$^b$)—Ar, An⁻ | (Va) |
| Het⁺—N(R$^a$)—N=C(R$^b$)—Ar, An⁻ | (V'a) |
| Het⁺—N=N—Ar, An⁻ | (VIa) |
| Ar⁺—N=N—Ar', An⁻ | (VI'a) and |
| Het⁺—N=N—Ar'—N=N—Ar, An⁻ | (VIIa) | in which formulas (Va), (V'a), (VIa), (VI'a) and (VIIa):
Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;
Ar⁺ representing an aryl radical, such as phenyl or naphthyl, bearing an exocyclic cationic charge, preferentially ammonium, particularly tri($C_1$-$C_8$)alkylammonium such as trimethylammonium;
Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;
Ar' is an optionally substituted divalent (hetero)arylene group such as phenylene, particularly para-phenylene, or naphthalene, which are optionally substituted, preferentially with one or more groups $(C_1$-$C_8)$alkyl, hydroxyl or $(C_1$-$C_8)$alkoxy;

Ar" is an optionally substituted (hetero)aryl group such as phenyl or pyrazolyl, which are optionally substituted, preferentially with one or more groups $(C_1$-$C_8)$alkyl, hydroxyl, (di)$(C_1$-$C_8)$(alkyl)amino, $(C_1$-$C_8)$alkoxy or phenyl;

$R^a$ and $R^b$, which may be identical or different, represent a hydrogen atom or a group $(C_1$-$C_8)$alkyl, which is optionally substituted, preferentially with a hydroxyl group;

or alternatively the substituent $R^a$ with a substituent of Het$^+$ and/or $R^b$ with a substituent of Ar and/or $R^a$ with $R^b$ form, together with the atoms that bear them, a (hetero)cycloalkyl;

particularly, $R^a$ and $R^b$ represent a hydrogen atom or a group $(C_1$-$C_4)$alkyl, which is optionally substituted with a hydroxyl group;

An$^-$ represents an anionic counter-ion such as mesylate or halide.

In particular, mention may be made of the azo and hydrazono cationic dyes bearing an endocyclic cationic charge of formulae (Va), (V'a) and (Via) as defined previously. More particularly those of formulae (Va), (V'a) and (Via) derived from the dyes described in patent applications WO 95/15144, WO 95/01772 and EP-714954.

Preferentially, the cationic part is derived from the following derivatives:

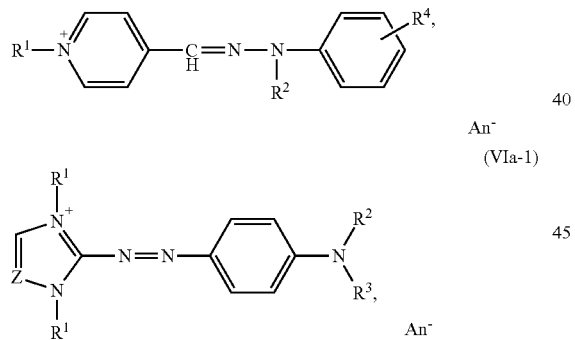

formulae (V-1) and (VI-1) with:

$R^1$ representing a $(C_1$-$C_4)$ alkyl group such as methyl;

$R^2$ and $R^3$, which are identical or different, represent a hydrogen atom or a $(C_1$-$C_4)$alkyl group, such as methyl; and $R^4$ represents a hydrogen atom or an electron-donating group such as optionally substituted $(C_1$-$C_8)$alkyl, optionally substituted $(C_1$-$C_8)$alkoxy, or (di)$(C_1$-$C_8)$(alkyl)amino optionally substituted on the alkyl group(s) with a hydroxyl group; particularly, $R^4$ is a hydrogen atom, Z represents a CH group or a nitrogen atom, preferentially CH;

An$^-$ represents an anionic counter-ion such as mesylate or halide.

The dye of formulae (Va-1) and (VIa-1) can be chosen from Basic Red 51, Basic Yellow 87 and Basic Orange 31 or derivatives thereof:

Basic Red 51

Basic Orange 31

Basic Yellow 87

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the one or more direct dyes more particularly represent from about 0.001% to 10% by weight, such as from about 0.005% to 5% by weight, of the total weight of the system or composition comprising the system in which it is present.

Alkalizing Agents

In some embodiments, the hair-color altering composition comprises an alkalizing agent. The alkalizing agent the present invention may be chosen from organic amines, organic amine salts, ammonium salts, inorganic bases, and hydroxide base compounds.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkylamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other organic amines correspond to the formula (IV):

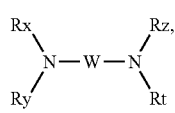

wherein W is chosen from C1-C6 alkylene residues optionally substituted with a hydroxyl group or a C1-C6 alkyl radical; Rx, Ry, Rz and Rt, which may be identical or different, are chosen from a hydrogen atom, C1-C6 alkyl radicals, C1-C6 hydroxyalkyl radicals, and C1-C6 aminoalkyl radicals.

Examples of such amines that may be mentioned include but not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Such basic amino acids may be chosen from those corresponding to formula (A) below:

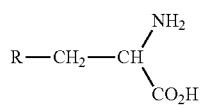

wherein R is a group chosen from:

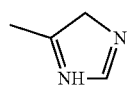

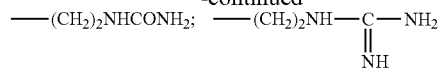

The compounds corresponding to formula (A) may be chosen from histidine, lysine, arginine, ornithine, and citrulline.

Amino acids that may be used in the present disclosure include but not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amines are chosen from basic amino acids. The amino acids may be chosen from, for instance, arginine, lysine and histidine, or mixtures thereof.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

As a non-limiting example, the organic amines are chosen from alkanolamines. For example, the organic amines are chosen from ethanolamine, triethanoloamine, 2-amino-2-methyl-1-propanol (amino methyl propanol), or preferably from 2-amino-2-methyl-1-propanol and monoethanolamine, or mixtures thereof. Further as an example, the organic amine is monoethanolamine.

The alkalizing agent may be an organic amine in salt form. The term "organic amine salt," as used herein, means organic or mineral salts of an organic amine as described above.

As a non-limiting example, the organic salts may be chosen from the salts of organic acids, such as citrates, lactates, glycolates, gluconates, acetates, propionates, fumarates, oxalates and tartrates.

Further as a non-limiting example, the mineral salts may be chosen from hydrohalides (for example hydrochlorides), carbonates, hydrogen carbonates, sulfates, hydrogen phosphates, and phosphates.

The ammonium salts that may be used according to the present disclosure may be chosen from the following acid salts: carbonate, bicarbonate. For instance, the salt is the carbonate, such as ammonium carbonate.

The inorganic bases that may be used may be chosen from alkali metal phosphates and carbonates such as, for example, sodium phosphate, potassium phosphate, sodium carbonate, sodium bicarbonate, potassium carbonate, potassium bicarbonate, and their derivatives.

The inorganic bases may also include alkali metals of carboxylates such as, for example, sodium acetate, potassium acetate, sodium citrate, and potassium citrate, and their derivatives.

The hydroxide base compounds can be chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the alkalizing agent is chosen from alkali metal carbonates, alkali metal phosphate, organic amines, hydroxide base compounds, and derivatives thereof.

According to at least one embodiment, the alkalizing agent is chosen from aminomethyl propanol, aminomethyl propanediol, triisopropanol amine sodium hydroxide, potassium hydroxide, ammonium hydroxide, dimethylstearylamine, dimethyl/tallowamine lysine, ornithine, arginine, monoethanolamine, triethanolamine, calcium hydroxide, calcium bicarbonate, sodium bicarbonate, and mixtures thereof According to one embodiment, the alkalizing agent is chosen from at least one organic amine such as at least one alkanolamine. A particularly preferred alkanolamine is ethanolamine (also known as monoethanolamine or MEA).

According to one embodiment, the alkalizing agent is chosen from at least one hydroxide base compounds, a particularly preferred hydroxide base compounds is ammonium hydroxide, According to one embodiment, the alkalizing agent comprises ammonium hydroxide and ethanolamine.

The at least one alkalizing agent of the present invention may be employed in an amount of from about 2% to about 20% by weight, such as from about 2% to about 11% by weight, and further such as from about 4.5% to about 10% by weight, based on the total weight of the hair color composition of the present invention, including increments and ranges therein there between.

The total amount of the alkalizing agent in the present invention may be employed in an amount of from about 2, 3, 4, 5, 6, 7, 8, 9, 10, 11, 12, 13, 14, 15, 16, 17, 18, 19, to about 20 percent by weight, including increments and ranges therein there between.

The amount of the alkalizing agent in the composition can be such that the pH of the composition can be neutral or alkaline range pH above 7.

According to at least one embodiment, the compositions or compositions for altering the color of keratin fibers of the present invention contain a small amount (i.e., greater than 0 but less than 8, 7, 6, 5, 4, 3 or 2% by weight) of ammonia, or is substantially free of ammonia.

According to another embodiment, the compositions or compositions for altering the color of keratin fibers of the present invention contain ammonia/ammonium hydroxide in an amount such that it is used as the alkalizing agent in the compositions.

Fatty Substances

Fatty substances (also referred to interchangeably as "fatty compounds") may be included in one or more embodiments of the invention. In some embodiments, two or more fatty substances may be included. In further embodiments, such fatty substances may be a fatty substance other than a fatty acid. As used herein, "fatty substance" means an organic compound insoluble in water at normal temperature (25° C.) and at atmospheric pressure (760 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

Fatty substances are, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the composition of the disclosure, include: esters of a glycerol oligomer, in particular diglycerol esters, especially condensates of adipic acid and of glycerol, for which a portion of the hydroxyl groups of the glycerols has reacted with a mixture of fatty acids, such as stearic acid, capric acid, isostearic acid and 12-hydroxystearic acid, such as in particular those sold under the brand name Softisan 649 by Sasol; arachidyl propionate, sold under the brand name Waxenol 801 by Alzol; fatty acid triglycerides and their derivatives; pentaerythritol esters; esters of dimer diol and dimer diacid, if appropriate esterified on their free alcohol or acid functional group(s) by acid or alcohol radicals, in particular dimer dilinoleate esters; such esters can be chosen in particular from esters with the following INCI nomenclature: bis-behenyl/isostearyl/phytosteryl dimer dilinoleyl dimer dilinoleate (Plandool G), phytosteryl isostearyl dimer dilinoleate (Lusplan PI-DA or Lusplan PHY/IS-DA), phytosteryl/isostearyl/cetyl/stearyl/behenyl dimer dilinoleate (Plandool H or Plandool S), and their mixtures; mango butter, such as that sold under the reference Lipex 203 by AarhusKarlshamn; hydrogenated soybean oil, hydrogenated coconut oil, hydrogenated rapeseed oil or mixtures of hydrogenated vegetable oils, such as the soybean, coconut, palm and rapeseed hydrogenated vegetable oil mixture, for example the mixture sold under the reference Akogel® by AarhusKarlshamn (INCI name: Hydrogenated Vegetable Oil); shea butter, in particular that having the INCI name Butyrospermum Parkii Butter, such as that sold under the reference Sheasoft® by AarhusKarlshamn; cocoa butter, in particular that which is sold under the name CT Cocoa Butter Deodorized by Dutch Cocoa BV or that which is sold under the name Beurre De Cacao NCB HD703 758 by Barry Callebaut; shorea butter, in particular that which is sold under the name Dub Shorea T by Stearinerie Dubois; and their mixtures.

According to a preferred embodiment, the fatty substance is chosen from hydrogenated vegetable oil, shea butter, cocoa butter, shorea butter, a soybean, coconut, palm and rapeseed hydrogenated vegetable oil mixture, and their mixtures, and more particularly those referenced above.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoro-methoxybutane and nonafluoroethoxyisobutane; derivatives of perfluoromorpholine, such as 4-trifluoromethyl perfluoromorpholine sold under the name "PF 5052®" by the 3M Company. The non-silicone oils of the present invention may be employed in an amount of from about 0.5% to about 5% by weight, such as from about 1% to about 5.5% by weight, and further such as from about 1.5% to about 4% by weight, based on the total weight of the hair color composition of the present invention, including increments and ranges therein there between.

The total amount of the non-silicone oils in the present invention may be employed in an amount of from about 0.5, 0.6, 0.7, 0.8, 0.9, 1, 2, 3, 4, to about 5 percent by weight, including increments and ranges therein there between.

As used herein, "fatty alcohol" refers to any alcohol with a carbon chain of C5 or greater, such as, for example, C8 or greater, C10 or greater, and C12 or greater. The at least one fatty alcohol may be chosen from, for example, C9-C11 alcohols, C12-C13 alcohols, C12-C15 alcohols, C12-C16 alcohols, C14-C15 alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

As used herein, "alkoxylated fatty alcohol" refers to any fatty alcohol with a carbon chain of C5 or greater, as defined above, further comprising at least one alkoxy group. For example, the at least one alkoxylated fatty alcohol may have a carbon chain of C8 or greater, C10 or greater, and C12 or greater. Further, for example, the at least one alkoxylated fatty alcohol may be chosen from alkoxylated polymers (including co-, ter- and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

Non-limiting examples of the at least one alkoxylated fatty alcohol include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetyl-steareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C 11-C15 pareth-20, C12-C15 pareth-9, C12-C15 pareth-12, and C22-C24 pareth-33.

The fatty alcohols usable as fatty substances in the composition of the disclosure include, but are not limited to, non-alkoxylated, saturated or unsaturated, linear or branched, and have from 6 to 30 carbon atoms and more particularly from 8 to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched C1-C26 aliphatic mono- or polyacids and of saturated or unsaturated, linear or branched C1-C26 aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of C4-C22 di- or tricarboxylic acids and of C1-C22 alcohols and the esters of mono-, di- or tricarboxylic acids and of C2-C26 di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; glycol distearates; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of C6-C30, such as C12-C22 fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated C6-C30, such as C12-C22 fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

Surfactants

In some embodiments, the hair color-altering compositions comprise at least one surfactant selected from anionic surfactants, nonionic surfactants and mixtures thereof.

The total amount of the one or more surfactants included in the hair color-altering compositions can vary, especially depending on the type of hair color-altering composition in with they are contained. The total amount of the one or more surfactants is typically about 0.1 to about 40 wt. %, based on the total weight of the hair color-altering composition, including all ranges and subranges therebetween. In some cases, the total amount of the one or more surfactants is about 0.1 to about 35 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.1 to about 5 wt. %, about 0.5 to about 40 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 0.5 to about 5 wt. %, about 1 wt. % to about 40 wt. %, about 1 wt. % to about 30 wt. %, about 1 wt. % to about 20 wt. %, about 1 wt. % to about 15 wt. %, about 1 wt. % to about 10 wt. %, or about 1 wt. % to about 5 wt. %.

Anionic Surfactants

The term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$.

The hair color-altering compositions may include one or more anionic surfactants. Non-limiting examples of anionic surfactants include alkyl sulfates, alkyl ether sulfates, acyl isethionates, acyl glycinates, acyl taurates, acyl amino acids, acyl sarcosinates, sulfosuccinates, sulfonates, and a mixture thereof, wherein the alkyl and acyl groups of all these compounds comprise from 6 to 24 carbon atoms. In some cases, anionic sulfate surfactants may be excluded from the one or more anionic surfactants. In such cases, the one or more anionic surfactants may be selected from the group consisting of acyl isethionates, acyl glycinates, acyl taurates, acyl amino acids, acyl sarcosinates, sulfosuccinates, sulfonates, and a mixture thereof, wherein the alkyl and acyl groups of all these compounds comprise from 6 to 24 carbon atoms. A more exhaustive list of anionic surfactants that may be included in the hair color-altering compositions is provided later, under the heading "Anionic Surfactants."

The total amount of the one or more anionic surfactants may be about 1 to about 40 wt. %, based on the total weight of the hair color-altering composition, including all ranges and subranges therebetween. Furthermore, the total amount of the one or more anionic surfactants may be about 1 to about 35 wt. %, about 1 to about 30 wt. %, about 5 wt. % to about 40 wt. %, about 5 wt. % to about 25 wt. %, about 5 wt. % to about 30 wt. %, about 10 wt. % to about 40 wt. %, about 10 wt. % to about 35 wt. %, or about 15 wt. % to about 40 wt. %.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of $(C_6$-$C_{24})$alkyl sulfates, $(C_6$-$C_{24})$alkyl ether sulfates, which are optionally ethoxylated, comprising from 2 to 50 ethylene oxide units, and a mixture thereof, in particular in the form of alkali metal salts or alkaline-earth metal salts, ammonium salts or amino alcohol salts. More preferentially, the anionic surfactant(s) are chosen from $(C_{10}$-$C_{20})$alkyl ether sulfates, and in particular sodium lauryl ether sulfate.

Non-Ionic Surfactants

Non-ionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The total amount of the one or more non-ionic surfactants may be about 1 to about 40 wt. %, based on the total weight of the hair color-altering composition, including all ranges and subranges therebetween. Furthermore, the total amount of the one or more non-ionic surfactants may be about 1 to about 35 wt. %, about 1 to about 30 wt. %, about 5 wt. % to about 40 wt. %, about 5 wt. % to about 25 wt. %, about 5 wt. % to about 30 wt. %, about 10 wt. % to about 40 wt. %, about 10 wt. % to about 35 wt. %, or about 15 wt. % to about 40 wt. %.

The non-ionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a mixture thereof, and are preferably oxyethylene units.

Examples of oxyalkylenated nonionic surfactants that may be mentioned include: [0115] oxyalkylenated ($C_8$-$C_{24}$) alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

As examples of polyglycerolated nonionic surfactants, polyglycerolated $C_8$-$C_{40}$ alcohols are preferably used. In particular, the polyglycerolated $C_8$-$C_{40}$ alcohols correspond to the following formula:

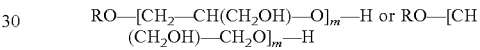

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Preferably, the nonionic surfactant may be a nonionic surfactant with an HLB of 18.0 or less, such as from 4.0 to 18.0, more preferably from 6.0 to 15.0 and furthermore preferably from 9.0 to 13.0. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Cationic Polymer

In some instances, the hair color-altering compositions include one or more cationic polymers. Non-limiting examples of cationic polymers include poly(methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium -91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

The total amount of the one or more cationic polymers, when included in the hair color-altering composition, is typically about 0.01 to about 15 wt. %, based on the total weight of the composition, including all ranges and subranges therebetween. The total amount of the one or more cationic polymers may be about 0.01 to about 8 wt. %, about 0.01 to about 6 wt. %, about 0.01 to about 5 wt. %, about 0.05 to about 8 wt. %, about 0.05 to about 6 wt. %, about 0.05 to about 5 wt. %, about 0.1 to about 10 wt. %, about 0.1 to about 8 wt. %, about 0.1 to about 6 wt. %, or about 0.1 to about 5 wt.

Solvent

In one or more embodiments, the hair color-altering compositions described herein comprise a solvent. In some embodiments, the solvent comprises water. The total amount of water in the hair color-altering compositions may vary depending on the type of composition and the desired consistency, viscosity, etc. In some cases, the total amount of water is about 50 to 95 wt. %, based on the total weight of the hair color-altering composition, including all ranges and subranges therebetween. The total amount of water may be about 50 to about 90 wt. %, about 50 to about 85 wt. %, about 60 to 95 wt. %, about 60 to 90 wt. %, about 60 to about 85 wt. %, greater than 60 to about 95 wt. %, greater than 60 to about 90 wt. %, greater than 60 to about 85 wt. %, about 65 to about 95 wt. %, about 65 to about 90 wt. %, about 65 to about 85 wt. %, about 70 to about 95 wt. %, or about 70 to about 90 wt. %. In some instances, the total amount of water is greater than 60 wt. %. For example, the total amount of water may be at least 61, 62, 63, 64, 65, 66, 67, 68, 69, or 70 wt. % up to about 90 or about 95 wt. %. Likewise, the total amount of water may be at least 61, 62, 63, 64, 65, 66, 67, 68, 69, or 70 wt. % to about 95 wt. %, 61, 62, 63, 64, 65, 66, 67, 68, 69, or 70 wt. % to about 90 wt. %, or about 70 wt. % to about 90 wt. %.

In some embodiments, the composition may comprise other solvents, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the water-soluble solvents (which is separate than the water in the compositions) may vary, but in some cases are about 0.01 to about 50 wt. %, based on the total weight of the composition. The total amount of the water-soluble solvents (separate from the water in the compositions), is about 0.01 to about 40 wt. %, about 0.01 to about 30 wt. %, about 0.01 to about 20 wt. %, about 0.01 to about 10 wt. %, about 0.01 to about 5 wt. %, 0.1 to about 40 wt. %, about 0.1 to about 30 wt. %, about 0.1 to about 20 wt. %, about 0.1 to about 10 wt. %, or about 0.1 to about 5 wt. %.

Thickening Agent

In some embodiments, the hair color-altering composition further comprises a thickening agent. In other embodiments, the hair color-altering composition does not comprise a thickening agent.

The hair color-altering compositions may contain one or more thickeners (also referred to as thickening agents or viscosity modifying agents). Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair color-altering composition.

In some embodiments, the thickener is chosen from hydroxyethylcellulose, cetyl hydroxyethylcellulose, and combinations thereof.

The total amount of the one or more thickening agents may vary, but in some cases is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about wt. %, about 0.5 to about 5 wt. %, about 1 to about 10 wt. %, about 1 to about 8 wt. %, about 1 to about 6 wt. %, or about 1 to about 5 wt. %, based on the total weight of the composition.

Optional Components

The composition according to the disclosure can comprise any auxiliary or additional component suitable for use in cosmetic compositions, and in particular suitable for hair coloring or lightening compositions. Such components may include, but are not limited to, cosmetically acceptable solvents, silicone compounds, rheology modifying agents such as acrylic polymers, cationic, nonionic, amphoteric or zwitterionic surfactants or mixtures thereof, anionic, cationic, nonionic, amphoteric or zwitterionic polymers or mixtures, film forming agents or polymers, humectants and moisturizing agents, fatty substances other than the claimed fatty substances, emulsifying agents other than fatty substances, fillers, structuring agents, propellants, shine agents, conditioning agents, antioxidants or reducing agents, penetrants, sequestrants, fragrances, buffers, dispersants, conditioning agents, for instance volatile or non-volatile, modified or unmodified silicones, ceramides, preserving agents, opacifiers, sunscreen agents, and antistatic agents. Acids, for example citric acid, can affect the pH of the system resulting in loss of lift. As such, optional auxiliary or additional components will be chosen so as to minimize any detrimental effect to the advantages of the hair color bases and compositions described herein.

Exemplary auxiliary ingredients useful in the hair color composition according to various embodiments of the disclosure include, but are not limited to, rheology-modifying agents, bleach activators and co-bleach activators, direct dyes, chelants, fatty substances, ceramides, alkoxyamino-silicones, silanes, and lift-enhancing agents, such as nitrogen-containing compounds and metal catalyst compounds.

The composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the hair color composition in an amount effective with a pH of greater than 7.

The hair color-altering compositions of the instant disclosure may be free or essentially free of taurate surfactants and salts thereof. For example, the compositions may be free or essentially free of taurate surfactants and salts thereof, of the following formula:

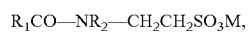

$$R_1CO\text{---}NR_2\text{---}CH_2CH_2SO_3M,$$

wherein $R_1$ denotes a saturated or unsaturated hydrocarbon group with an average number of carbon atoms of 7-19; $R_2$ denotes hydrogen or an alkyl group with an average number of carbon atoms of 1-3; and M denotes an alkali metal, alkali earth metal, ammonium, or organic amine or derivative. Specific examples include N-methyl cocoyl taurate and sodium cocoyl taurate.

The compositions of the disclosure may be free or essentially free of polyethylene glycol (PEG) and/or derivatives thereof and may be free or essentially free of propylene glycol (PPG) and/or derivatives thereof. For example, the compositions may be free or essentially free of polyethylene glycols having a molecular weight of 200-10,000, or polyethylene glycols having a molecular weight of 200-1,000. Furthermore, PEGylated surfactants may also be excluded from the hair color-altering compositions. Non-limiting examples of PEGylated surfactants include ethoxylated fatty esters.

Kits

Another aspect of the invention pertains to kits which comprise any of the hair color-altering agents described herein. In some embodiments, the kit further comprises a developer composition. The developer composition may be housed in a separate container from the hair color-altering composition, and may then be mixed prior to application onto hair.

In some embodiments, the developer composition is aqueous or is in the form of an emulsion. The developer composition can contain at least one solvent, chosen from water, organic solvents, and mixtures thereof.

In alternative embodiments, the developer composition is substantially anhydrous. The term "substantially anhydrous" means that the developer composition is either completely free of water or contains no appreciable amount of water, for example, no more than 5% by weight, or no more than 2% by weight, or no more than 1% by weight, based on the weight of the developer composition. It should be noted that this refers for example to bound water, such as the water of crystallization of the salts or traces of water absorbed by the raw materials used in the preparation of the compositions according to embodiments of the disclosure.

When the developer composition is substantially anhydrous, the developer composition may comprise at least one solvent chosen from organic solvents. Suitable organic solvents for use in the developer composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvents for use in the present invention can be volatile or non-volatile compounds. The organic solvent may, for example, be present in an amount ranging from about 0.5% to about 70% by weight, such as from about 2% to about 60% by weight, preferably from about 5 to about 50% by weight, relative to the total weight of the developer composition or system in which it is present.

The developer composition may be in the form of a powder, gel, liquid, foam, lotion, cream, mousse, and emulsion.

The pH of the developer composition can range from about 2 to about 12, such as from about 6 to about 11, and it may be adjusted to the desired value using acidifying/alkalizing agents that are well known in the art. In certain embodiments, the pH of the developer composition is below 7. The pH of the composition resulting from mixing together the hair color-altering composition and the developer composition may range from about 7, 8, 9, 10 or 11 to about 8, 9, 10, 11 or 12.

According to at least one embodiment, the system and/or compositions comprising the system and the developer composition are free or substantially free of ammonia.

Methods

Another aspect of the invention pertains to methods of using any of the compositions described herein. In one or more embodiments, the method comprises applying the hair color-altering composition to hair. The composition may be left on the hair for a period of time sufficient to achieve the desired alteration in hair tone. For example, the hair color composition may be left on the hair for up to one hour, such as from about 3 minutes to about 45 minutes, from about 5 minutes to about 30 minutes, or from about 10 minutes to about 20 minutes. In further embodiments, the hair color composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the hair color composition on the hair in order to achieve the desired alternation in hair tone. By way of non-limiting example, various embodiments according to the disclosure may provide for an increase of 1 to 4 in the tone height of the hair. In some embodiments, the hair color-altering composition is mixed with a developer composition prior to application to hair. If desired, the composition may, optionally, be shampooed and/or rinsed off the hair.

EXAMPLES

Implementation of the present disclosure is provided by way of the following examples. The examples serve to illustrate the technology without being limiting in nature.

Example 1

Three formulas were prepared with the ingredients shown below in Table 1. Comparative Example 1 is comparative for at least the reason it does not contain citric acid. Examples 2 and 3 are inventive. The three formulas were in the form of a cream.

TABLE 1

| | INCI US | Comp. Ex. 1 wt. % | Inv. Ex. 2 wt. % | Inv. Ex. 3 wt. % |
|---|---|---|---|---|
| FATTY COMPOUND | OLEYL ALCOHOL | 2 | 2 | 2 |
| NONIONIC SURFACTANT | DECETH-3 | 2.7 | 2.7 | 2.7 |
| FRAGRANCE | FRAGRANCE | 0.75 | 0.75 | 0.75 |
| AMINO ACID | TAURINE | | | 2.16 |
| ANIONIC SURFACTANT | OLEIC ACID | 2.7 | 2.7 | 2.7 |
| THICKENER | CETYL HYDROXYETHYL-CELLULOSE | 0.15 | 0.15 | |
| ALKALIZING AGENT | AMMONIUM HYDROXIDE | 8.1477 | 8.1477 | 8.1477 |
| ALKALIZING AGENT | ETHANOLAMINE | 0.63 | 3 | 3.78 |
| CATIONIC POLYMER | POLY-QUATERNIUM-6 | 0.64 | 0.64 | 0.64 |
| FATTY COMPOUND | GLYCOL DISTEARATE | 3 | 3 | 2 |
| FATTY COMPOUND | CETEARYL ALCOHOL | 16 | 16 | 3 |
| MISC. (COLORANT, ANTISTATIC, CHELANT, ANTIOXIDANT) | MISC. | 2.27 | 2.27 | 2.27 |
| SOLVENT | WATER | 53.7123 | 48.8423 | 59.5423 |
| CARBOXYLIC ACID | CITRIC ACID | | 2.5 | 3.31 |
| FATTY COMPOUND | MINERAL OIL | 3 | 3 | 3 |
| THICKENER | HYDROXYETHYL-CELLULOSE | 0.3 | 0.3 | |

Thermo-rheology measurements were taken of the three formulas, and the evolution of elastic modulus (G') measured as a function of time and temperature. These plots are shown in FIG. 1A-B. As seen from the figures, the G' of Comparative Example 1 dropped significantly as temperature increased, although it remained relatively stable with respect to time. Inventive Example 2 decreased somewhat with increased temperature, as well as changed the least with respect to time. Inventive Example 3 remained fairly constant with respect to both temperature and time. This indicates an increase in stability in the two inventive formulas.

Example 2

|  | INCI U.S. | B wt. % | C wt. % | D wt. % | E wt. % | F wt. % |
|---|---|---|---|---|---|---|
| Amino Acid | TAURINE | 0.03 | 0.1 | 0.01 | 0.08 | 0.06 |
| Carboxylic Acid | CITRIC ACID | 0.6 | 0.9 | 1.2 | 1.4 | 1.7 |
| Alkalizing Agent | AMMONIUM HYDROXIDE | 5.8 | 5.8 | 5.8 | 5.8 | 5.8 |
|  | ETHANOLAMINE | 7 | 7.1 | 7.3 | 7.4 | 7.5 |
|  | SODIUM METABISULFITE | 0.7 | 0.7 | 0.7 | 0.7 | 0.7 |
| Colorants | 6-HYDROXYINDOLE, TOLUENE-2,5-DIAMINE, m-AMINOPHENOL, p-AMINOPHENOL, 2-METHYLRESORCINOL, TITANIUM DIOXIDE, AND/OR RESORCINOL | ≤2 | ≤2 | ≤2 | ≤2 | ≤2 |
| Fatty Compounds | GLYCOL DISTEARATE, CETEARYL ALCOHOL, OLEYL ALCOHOL, AND/OR HYDROGENATED VEG. OIL | 26 | 24.5 | 26 | 24.5 | 26 |
| Cationic Polymer | POLYQUATERNIUM-6 | 0.4 | 0.4 | 0.4 | 0.4 | 0.4 |
| Nonionic Surfactant | LAURETH-12 AND/OR OLETH-30 | 9 | 6 | 6 | 9 | 6 |
| Anionic Surfactant | OLEIC ACID | 2 | 2 | 2 | 2 | 2 |
| Polymer | HEXADIMETHRINE CHLORIDE | 0.6 | 0.6 | 0.6 | 0.6 | 0.6 |
| Thickener | CETYL HYDROXYETHYL-CELLULOSE AND/OR HYDROXYETHYL-CELLULOSE | 0.3 | 0.3 | 0.3 | 0.3 | 0.3 |
| Miscellaneous | Preservative(s), Fragrance, pH adjuster(s), etc. | ≤3 | ≤3 | ≤3 | ≤3 | ≤3 |
| Water | WATER | QS 100 | QS 100 | QS 100 | QS 100 | QS 100 |

Compositions B-F were prepared and their performance compared with a commercial benchmark product. Hair tresses of highly bleached Caucasian hair (1 g/27 cm) of approximately fifty hair fibers were treated three times as outlined below, and then subjected to testing using a Miniature Tensile Tester (MTT). The commercial benchmark product and each of Compositions B-F were mixed with 40V developer composition in a ratio of 1:2 (Benchmark/Compositions B-F: Developer Composition). 8 grams of the commercial benchmark product or Composition B-F was mixed with 16 grams of 40V developer composition and each of the mixtures were used to treat two hair tresses. The mixtures were applied to the hair tresses and allowed to process for 50 minutes. After 50 minutes of processing, the hair tresses were rinsed and then shampooed three times. After being shampooed three times, the hair tresses were blow dried. The process was repeated two more times, i.e., the entire hair coloring process was carried out for a total of three times. The tresses were then subjected to break stress testing and to elastic modulus testing.

Break Stress Testing

Figure 2:
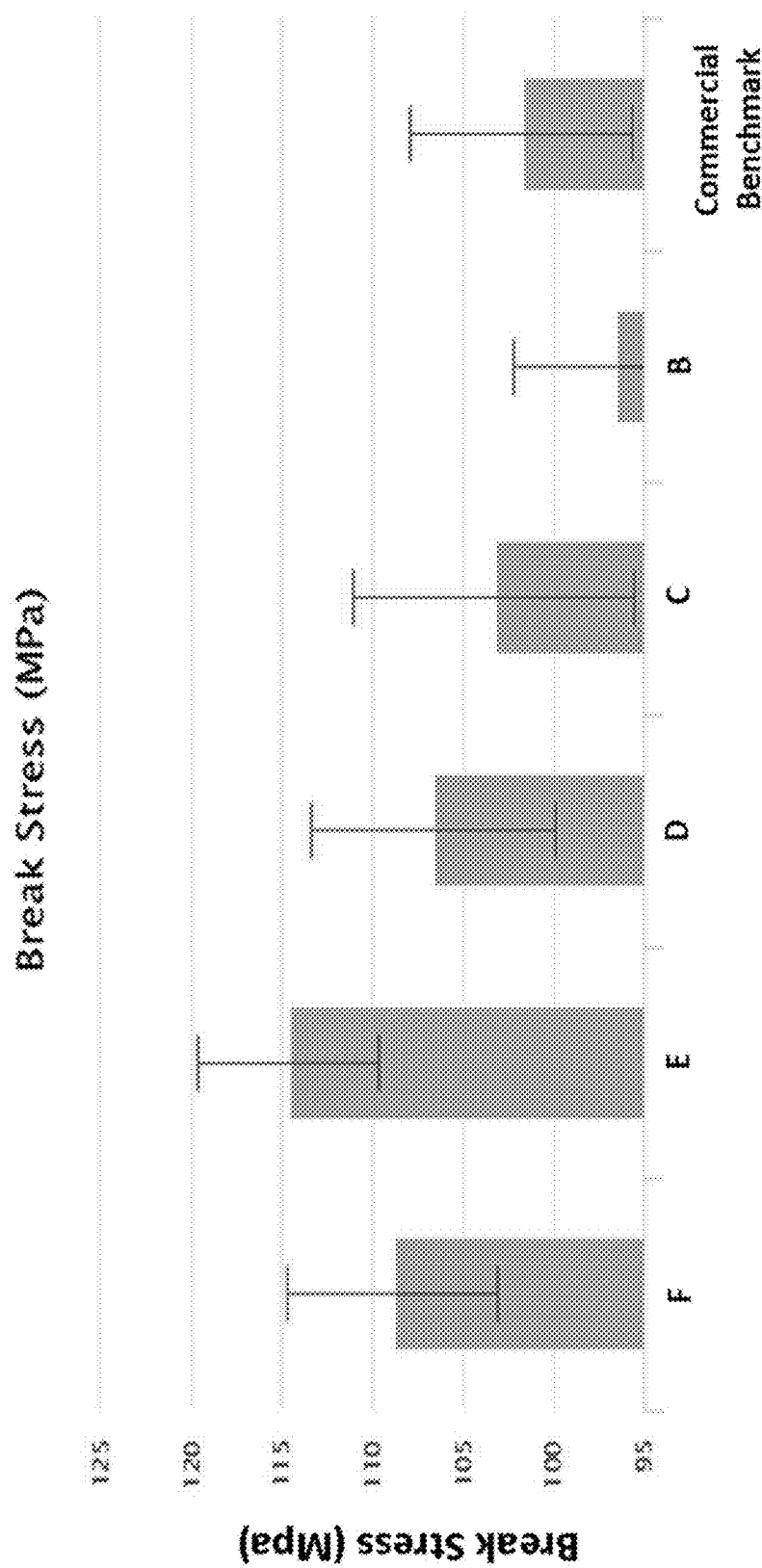
FIG. 2 is a graph showing the break stress of hair treated with compositions according to the instant disclosure (B-F) and hair treated with a commercial benchmark product.

The break stress represents the force/area needed to break the hair fiber. A higher break stress represents a stronger and stiffer hair fiber. The hair tresses treated as set forth above were subjected to break stress testing. The results are provided in the table below, and graphically presented in FIG. 2.

| Composition | Break Stress (MPa) | StdDev | Count |
|---|---|---|---|
| Composition E | 114.6 | 17.92 | 49 |
| Commercial Benchmark | 101.7 | 21.31 | 46 |
| Composition B | 96.48 | 20.25 | 48 |
| Composition F | 108.8 | 20.42 | 48 |
| Composition D | 106.6 | 22.59 | 43 |
| Composition C | 103.3 | 27.71 | 49 |

Treatment with Composition E resulted in a statistically higher break stress compared to the commercial benchmark product. Treatment with Compositions B, C, D, and F resulted in a break stress that was similar to treatment with the commercial benchmark product. There was no statistical difference in break stress for hair tresses treated with Compositions B, C, D, and F compared to hair tresses treated with the commercial benchmark product.

Elastic Modulus Testing (Young's Modulus)

Figure 3:
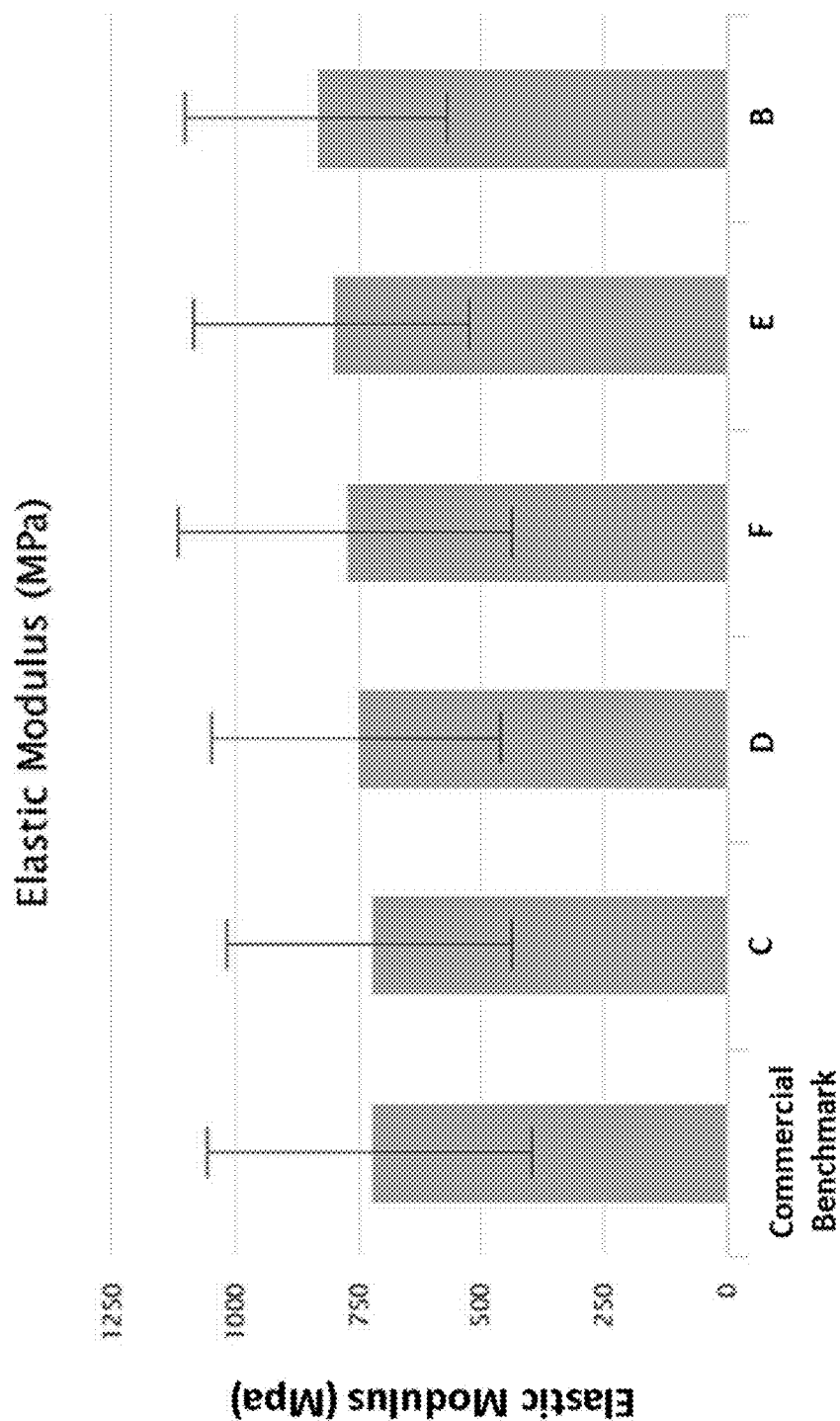
FIG. 3 is a graph showing the Young's modulus (the elastic modulus) of hair treated with compositions according to the instant disclosure (B-F) and hair treated with a commercial benchmark product.

The Young's modulus represents a measure of the hair's spring-like structure (elasticity). The mean Young's modulus for the hair tresses treated as set forth above was determined. The results are provided in the table below and graphically presented in FIG. 3.

| Composition | Elastic Modulus (MPa) | StdDev | Count |
|---|---|---|---|
| Commercial Benchmark | 725.1 | 331.4 | 46 |
| Composition F | 776.1 | 341.2 | 48 |
| Composition B | 833.2 | 267.2 | 48 |
| Composition E | 802.6 | 281.0 | 49 |

| Composition | Elastic Modulus (MPa) | StdDev | Count |
| --- | --- | --- | --- |
| Composition D | 753.0 | 293.7 | 43 |
| Composition C | 725.7 | 289.8 | 49 |

Treatment with Compositions B-F resulted in an elastic modulus that was similar to treatment with the commercial benchmark product. There was no statistical difference in elastic modulus for hair tresses treated with Compositions B-F compared to hair tresses treated with the commercial benchmark product.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts, for example, the salts of the amino acids, the amino sulfonic acids, and the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat" (and its grammatical variations) as used herein also refers to contacting keratinous substrates such as hair with the compositions of the present disclosure.

A "rinse-off" product refers to a composition such as a hair color-altering composition that is rinsed and/or washed with water either after or during the application of the composition onto the keratinous substrate, and before drying and/or styling said keratinous substrate. At least a portion, and typically most, of the composition is removed from the keratinous substrate during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair color-altering composition comprising:
about 0.01 wt. % to about 10 wt. % of taurine;
about 1 wt. % to about 10 wt. % of citric acid;
at least one oxidative dye selected from oxidation bases, couplers, or combinations thereof;
about 7 wt. % to about 10 wt. % of monoethanolamine;
about 5 wt. % to about 20 wt. % of ammonium hydroxide;
about 1 wt. % to about 5 wt. % of oleic acid; and
water.

2. The hair color-altering composition of claim 1, wherein the taurine is present in an amount ranging from about 0.01 wt. % to about 5 wt. %.

3. The hair color-altering composition of claim 1, wherein the oleic acid is present in an amount ranging from about 1 wt. % to about 2.7 wt. %.

4. The hair color-altering composition of claim 1, further comprising at least one fatty substance.

5. The hair color-altering composition of claim 4, wherein the at least one fatty substance is chosen from fatty alcohols, alkoxylated fatty alcohols, fatty acid esters, plant oils, or mixtures thereof.

6. The hair color-altering composition of claim 1 further comprising at least one non-ionic surfactant.

7. The hair color-altering composition of claim 1, further comprising one or more additional alkalizing agents selected from alkali metal carbonates, alkali metal phosphates, organic amines, hydroxide base compounds, or combinations thereof.

8. The hair color-altering composition of claim 1 comprising:
one or more cationic polymers.

9. The hair color-altering composition of claim 8, wherein the one or more cationic polymers are selected from the group consisting of poly(methacryloyloxyethyl trimethylammonium chloride), polyquaternium-37, quaternized cellulose derivatives, polyquaternium-4, polyquaternium-6, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and mixtures thereof.

10. A hair color-altering composition comprising:
about 0.05 wt. % to about 1 wt. % of taurine;
about 1 wt. % to about 2 wt. % of citric acid;
at least one oxidative dye selected from oxidation bases, couplers, or combinations thereof;
at least two alkalizing agents chosen from monoethanolamine and ammonium hydroxide, wherein the total amount of alkalizing agents ranges from 10 wt. % to about 20 wt. %;
about 1 wt. % to about 5 wt. % of oleic acid; and
water,
wherein the composition has a pH greater than 7, and
wherein the composition is essentially free of oxidizing agents.

11. The hair color-altering composition according to claim 10, further comprising at least one non-ionic surfactant.

12. The hair color-altering composition according to claim 10, further comprising at least one cationic polymer.

13. The hair color-altering composition according to claim 10, further comprising at least one fatty substance.

14. The hair color-altering composition according to claim 13, wherein the fatty substance is chosen from fatty alcohols, alkoxylated fatty alcohols, fatty acid esters, plant oils, or mixtures thereof.

15. The hair color-altering composition according to claim 10, further comprising at least one non-ionic surfactant, at least one cationic polymer, and at least one fatty substance chosen from fatty alcohols, alkoxylated fatty alcohols, fatty acid esters, plant oils, or mixtures thereof.

16. The hair color-altering composition according to claim 10, comprising from about 7 wt. % to about 10 wt. % monoethanolamine, and about 4.5 wt. % to about 10 wt. % of ammonium hydroxide.

17. A hair color-altering composition comprising:
about 0.01 wt. % to about 1 wt. % of taurine;
about 0.04 wt. % to about 2 wt. % of citric acid;
at least one oxidative dye selected from oxidation bases, couplers, or combinations thereof;
at least two alkalizing agents chosen from monoethanolamine and ammonium hydroxide, wherein the total amount of alkalizing agents ranges from 4.5 wt. % to about 10 wt. %;
about 1 wt. % to about 5 wt. % oleic acid;
at least one oxidizing agent; and
water.

18. The hair color-altering composition according to claim 17, further comprising at least one non-ionic surfactant.

19. The hair color-altering composition according to claim 17, further comprising at least one cationic polymer.

20. The hair color-altering composition according to claim 17, further comprising at least one fatty substance.

* * * * *